(12) United States Patent
Webb et al.

(10) Patent No.: US 11,793,422 B2
(45) Date of Patent: Oct. 24, 2023

(54) SENSING SYSTEM FOR RESPIRATOR

(71) Applicant: 3M INNOVATIVE PROPERTIES COMPANY, St. Paul, MN (US)

(72) Inventors: Richard C. Webb, St. Paul, MN (US); Andrew S. Viner, Roseville, MN (US); Nicholas G. Amell, Burnsville, MN (US); Andrew P. Bonifas, Edmonton (CA); Neal A. Rakow, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 539 days.

(21) Appl. No.: 16/641,742

(22) PCT Filed: Aug. 28, 2018

(86) PCT No.: PCT/IB2018/056560
§ 371 (c)(1),
(2) Date: Feb. 25, 2020

(87) PCT Pub. No.: WO2019/043581
PCT Pub. Date: Mar. 7, 2019

(65) Prior Publication Data
US 2020/0237258 A1    Jul. 30, 2020

Related U.S. Application Data

(60) Provisional application No. 62/553,569, filed on Sep. 1, 2017.

(51) Int. Cl.
*A61B 5/08* (2006.01)
*A61B 5/00* (2006.01)
(Continued)

(52) U.S. Cl.
CPC .............. *A61B 5/082* (2013.01); *A61B 5/002* (2013.01); *A61B 5/0017* (2013.01); *A61B 5/097* (2013.01);
(Continued)

(58) Field of Classification Search
CPC ..... A61B 5/0017; A61B 5/002; A61B 5/0813; A61B 5/082; A61B 5/097; G01N 27/122;
(Continued)

(56) References Cited

U.S. PATENT DOCUMENTS

| 4,146,025 A | 3/1979 | Warncke |
| 4,307,061 A | 12/1981 | Sarholz |

(Continued)

FOREIGN PATENT DOCUMENTS

| CN | 101676714 | 3/2010 |
| CN | 101581685 | 5/2013 |

(Continued)

OTHER PUBLICATIONS

"Assigned Protection Factors for the Revised Respiratory Protection Standard" Occupational Safety and Health Administration (OSHA 3352-02), 2009, 51 pages.

(Continued)

*Primary Examiner* — Orlando Bousono
(74) *Attorney, Agent, or Firm* — Steven A. Bern

(57) ABSTRACT

A system includes a respirator, a sensor including a sensing element, and a reader configured to be in wireless communication with the sensor. The sensor is positioned substantially within an interior gas space of the respirator.

18 Claims, 18 Drawing Sheets

(51) Int. Cl.
*A61B 5/097* (2006.01)
*G01N 27/12* (2006.01)
*G01N 33/497* (2006.01)

(52) U.S. Cl.
CPC ......... *G01N 27/122* (2013.01); *G01N 33/497* (2013.01)

(58) Field of Classification Search
CPC ... G01N 33/497; A62B 27/00; A61M 16/0003
See application file for complete search history.

(56) References Cited

U.S. PATENT DOCUMENTS

| | | | |
|---|---|---|---|
| 4,832,011 A | 5/1989 | Busch | |
| 4,846,166 A | 7/1989 | Willeke | |
| 4,846,168 A | 7/1989 | Abiko | |
| 4,914,957 A | 4/1990 | Dougherty | |
| 5,303,701 A | 4/1994 | Heins | |
| 5,373,869 A | 12/1994 | Zdrok | |
| 5,659,296 A | 8/1997 | Debe | |
| 5,936,703 A | 8/1999 | Miyazaki | |
| 6,125,845 A | 10/2000 | Halvorsen | |
| 6,300,123 B1 | 10/2001 | Vadgama | |
| 6,612,306 B1 | 9/2003 | Mault | |
| 6,614,241 B2 | 9/2003 | Schmitt | |
| 6,634,210 B1 | 10/2003 | Bosch | |
| 6,955,170 B1 | 10/2005 | Mullins | |
| 7,465,425 B1 | 12/2008 | Sun | |
| 7,614,280 B1 | 11/2009 | Gardner | |
| 7,648,617 B2 | 1/2010 | Miyazaki | |
| 7,911,345 B2 | 3/2011 | Potyrailo | |
| 7,927,558 B2 | 4/2011 | Kirollos | |
| 7,969,307 B2 | 6/2011 | Peeters | |
| 8,011,368 B2 | 9/2011 | Crutchfield | |
| 8,033,159 B2 | 10/2011 | Fleischer | |
| 8,151,630 B1 | 4/2012 | Gardner | |
| 8,165,786 B2 | 4/2012 | Rhodes | |
| 8,192,523 B1 | 6/2012 | Kaufman | |
| 8,208,681 B2 | 6/2012 | Heller | |
| 8,276,587 B2 | 10/2012 | Zhang | |
| 8,456,308 B2 | 6/2013 | Nelson | |
| 8,528,559 B2 | 9/2013 | Crutchfield | |
| 8,542,023 B2 | 9/2013 | Potyrailo | |
| 8,573,199 B2 | 11/2013 | King | |
| 8,578,756 B2 | 11/2013 | Suzuki | |
| 8,677,803 B2 | 3/2014 | Hocken | |
| 8,707,761 B2 | 4/2014 | Maeda | |
| 8,708,708 B1 | 4/2014 | Carideo | |
| 8,823,401 B2 | 9/2014 | Roth | |
| 8,908,928 B1 | 12/2014 | Hansen | |
| 9,092,709 B2 | 7/2015 | Forster | |
| 9,340,683 B2 | 5/2016 | Jing | |
| 9,361,411 B2 | 6/2016 | Thiruvengada | |
| 9,389,260 B2 | 7/2016 | Potyrailo | |
| 9,527,336 B2 | 12/2016 | Mahli | |
| 9,586,223 B2 | 3/2017 | Bentvelsen | |
| 9,643,186 B1* | 5/2017 | Ahmad | B01L 3/52 |
| 10,209,212 B2 | 2/2019 | Ruhl et al. | |
| 2003/0208133 A1 | 11/2003 | Mault | |
| 2004/0230108 A1* | 11/2004 | Melker | A61B 5/6829 |
| | | | 128/204.23 |
| 2005/0252273 A1 | 11/2005 | Imoto | |
| 2006/0048783 A1 | 3/2006 | Liu | |
| 2006/0237310 A1 | 10/2006 | Patel | |
| 2007/0042505 A1 | 2/2007 | Israel | |
| 2007/0125164 A1 | 6/2007 | Zielinski | |
| 2007/0287191 A1 | 12/2007 | Stiene | |
| 2008/0202196 A1 | 8/2008 | Richardson | |
| 2008/0262370 A1* | 10/2008 | Varney | A61B 5/0836 |
| | | | 600/532 |
| 2009/0275852 A1 | 11/2009 | Oki | |
| 2009/0288504 A1 | 11/2009 | Eiwen | |
| 2010/0006432 A1 | 1/2010 | Miyazaki | |
| 2010/0050735 A1* | 3/2010 | Varney | G01N 27/121 |
| | | | 73/23.3 |
| 2010/0175699 A1* | 7/2010 | Varney | A61M 16/0672 |
| | | | 128/204.23 |
| 2010/0212670 A1 | 8/2010 | Amighi | |
| 2011/0132070 A1* | 6/2011 | Hietala | G01N 33/497 |
| | | | 73/25.02 |
| 2011/0138884 A1 | 6/2011 | Hanson | |
| 2011/0270085 A1 | 11/2011 | King | |
| 2012/0055815 A1 | 3/2012 | Truex | |
| 2012/0073359 A1 | 3/2012 | Hanson | |
| 2012/0103057 A1 | 5/2012 | Kimata | |
| 2012/0286958 A1 | 11/2012 | Dunbar | |
| 2013/0036793 A1 | 2/2013 | White | |
| 2013/0086978 A1 | 4/2013 | Montividas | |
| 2013/0257460 A1 | 10/2013 | Roth | |
| 2013/0282609 A1 | 10/2013 | Au | |
| 2013/0327335 A1 | 12/2013 | Ishikawa | |
| 2014/0094671 A1 | 4/2014 | Boock | |
| 2014/0095102 A1 | 4/2014 | Potyrailo | |
| 2014/0251859 A1 | 9/2014 | Weikart | |
| 2014/0273082 A1 | 9/2014 | Cremins | |
| 2014/0278320 A1 | 9/2014 | Wang | |
| 2014/0299193 A1 | 10/2014 | Kenney | |
| 2015/0116093 A1 | 4/2015 | Swager | |
| 2015/0146169 A1 | 5/2015 | Ye et al. | |
| 2016/0003769 A1 | 1/2016 | Roundhill | |
| 2016/0067531 A1 | 3/2016 | Pariseau | |
| 2016/0070851 A1 | 3/2016 | Wang | |
| 2016/0153884 A1 | 6/2016 | Han | |
| 2016/0166859 A1 | 6/2016 | Rachapudi | |
| 2016/0193486 A1 | 7/2016 | Walker | |
| 2016/0213955 A1 | 7/2016 | Curran | |
| 2016/0317848 A1 | 11/2016 | Zilberstein | |
| 2017/0028228 A1 | 2/2017 | Zhao | |
| 2017/0122931 A1 | 5/2017 | Carnahan | |
| 2017/0347960 A1* | 12/2017 | Falk | A61B 5/1102 |
| 2017/0356899 A1 | 12/2017 | Güder | |
| 2018/0008849 A1 | 1/2018 | Baker | |
| 2018/0024038 A1 | 1/2018 | Shimokawa | |
| 2018/0078798 A1 | 3/2018 | Fabian | |
| 2018/0311517 A1 | 11/2018 | Patil et al. | |
| 2019/0001117 A1* | 1/2019 | Ben-David | A61B 5/4812 |
| 2019/0275359 A1 | 9/2019 | Shen | |
| 2020/0230444 A1 | 7/2020 | Viner | |
| 2020/0269076 A1 | 8/2020 | Farmer | |
| 2020/0370984 A1 | 11/2020 | Hashimoto | |

FOREIGN PATENT DOCUMENTS

| | | |
|---|---|---|
| CN | 203802905 | 9/2014 |
| CN | 108458841 A | 8/2018 |
| DE | 3914664 | 11/1990 |
| JP | 201402726 | 10/2014 |
| JP | 5652847 | 11/2014 |
| WO | WO 2005-113045 | 12/2005 |
| WO | WO 2008-028124 | 3/2008 |
| WO | WO 2009-103063 | 3/2011 |
| WO | WO 2011-163175 | 12/2011 |
| WO | WO 2012-128970 | 9/2012 |
| WO | WO 2013-028981 | 2/2013 |
| WO | WO 2013-144534 | 10/2013 |
| WO | WO 2014-138198 | 9/2014 |
| WO | WO 2014-150739 | 9/2014 |
| WO | WO 2015-050608 | 4/2015 |
| WO | WO 2016-044082 | 3/2016 |
| WO | WO 2016-065180 | 4/2016 |
| WO | WO 2016-195939 | 12/2016 |
| WO | WO 2017-069756 | 4/2017 |
| WO | WO 2017-120452 | 7/2017 |
| WO | 2019043581 A1 | 3/2019 |
| WO | WO 2019-043578 | 3/2019 |
| WO | WO 2019-043580 | 3/2019 |
| WO | WO 2019-046686 | 3/2019 |
| WO | WO 2019-046696 | 3/2019 |
| WO | WO 2019-046709 | 3/2019 |
| WO | WO 2019-046712 | 3/2019 |
| WO | WO 2019-160535 | 8/2019 |

(56) References Cited

FOREIGN PATENT DOCUMENTS

WO        2019172853 A1    9/2019
WO    WO 2019-224659      11/2019

OTHER PUBLICATIONS

Compernolle, "Henry's Law Constants of Polyols", Atmospheric Chemistry and Physics, Dec. 2014, vol. 14, No. 23, pp. 12815-12837.
Fouke, "Sensor for Measuring Surface Fluid Conductivity in Vivo" IEEE Transactions on Biomedical Engineering, Oct. 1988, vol. 35, No. 10, pp. 877-881.
"Global Sensor Market Forecast 2022: IoT and Wearables as Drivers", i-SCOOP, Jan. 2017, [retrieved from the internet on Apr. 20, 2020] URL <https://www.i-scoop.eu/global-sensor-market-forecast-2022/>, 5 pages.
Halberg, "Characterization of a Human Powered Nebulizer Compressor for Resource Poor Settings" BioMedical Engineering Online, Jun. 2014, Vo. 13, No. 77, 11 pages.
Litt, "Siloxane Zwitterions: Synthesis and Surface Properties of Crosslinked Polymers", Journal of Applied Polymer Science, 1975, Vo. 19, pp. 1221-1225.
"PIC16(L)F1503—14-Pin Flash, 8 Bit Microcontrollers" Microchip Technology Inc, Pub. No. ISBN: 978-1-63277-916-8, 2011-2015, 352 pages.
Product Literature: "PORTACOUNT® Respirator Fit Tester Model 8040 and Model 8048", A Product of TSI Inc. 2018, 8 pages.
Qiu, "Development and Evaluation of New Zwitterionic Hydrophilic Interaction Liquid Chromatography Stationary Phases Based on 3-P.P-diphenylphosphonium-Propylsufonate", Journal of Chromatography A, 2011, vol. 1218, No. 44, pp. 8075-8082.
Respirator Fit Testing, Cority, [retrieved from the internet on Feb. 22, 2019], URL <https://www.cority.com/ehsq-software/industrial-hygiene/respirator-fit-testing-ih/>, 2 pages.
"TSI Introduces Fitpro+ Fit Test Software", A.J. Abrams Company Inc., [retrieved from the internet on Feb. 22, 2019] URL <https://ajabrams.com/news/tsi-introduces-fitpro-fit-test-software>, 1 page.
International Search Report for PCT International Application No. PCT/IB2018/056557, dated Jan. 22, 2019, 4 pages.
International Search Report for PCT International Application No. PCT/IB2018/056559, dated Dec. 17, 2018, 3 pages.
International Search Report for PCT International Application No. PCT/IB2018/056560, dated Nov. 30, 2018, 5 pages.
International Search Report for PCT International Application No. PCT/US2018/049031, dated Nov. 15, 2018, 5 pages.
International Search Report for PCT International Application No. PCT/US2018/049052, dated Nov. 20, 2018, 3 pages.
International Search Report for PCT International Application No. PCT/US2018/049079, dated Jan. 11, 2019, 4 pages.
International Search Report for PCT International Application No. PCT/US2018/049082, dated Nov. 16, 2018, 3 pages.
Extended EP Search Report, EP18849930.5, dated May 11, 2021, 10 pages.
Extended EP Search Report, EP18851001.0, dated May 11, 2021, 10 pages.
Extended EP Search Report, EP18852636.2, dated May 11, 2021, 10 pages.
Don-Hee Hanab et al.: "Quantitative Fit Testing Techniques and Regulations for Tight-Fitting Respirators: Current Methods Measuring Aerosol or Air Leakage, and New Developments", AIHA Journal—American Industrial Hygiene Association Journal: a Publication for the Science of Occupational and Environmental Heal Th, American Industrial Hygiene Association, US, vol. 58, No. 3, Jan. 1, 1997 (Jan. 1, 1997), pp. 219-228, XP008165873,ISSN: 0002-8894, DOI: 10.1080/15428119791012874.
Extended EP Search Report, EP 18849497.5, dated Jun. 1, 2021, 9 pages.
Extended EP Search Report, EP 18849497.5, dated Jun. 1, 2021, 8 pages.
Extended EP Search Report, EP 18849687 .1, dated Jun. 1, 2021, 9 pages.
Extended EP Search Report, EP18851594.4, dated May 14, 2021, 8 pages.
Zhang, Sanitary Chemistry, ISBN 7-117-0013-9, Sep. 2, 1991.

\* cited by examiner

FIG. 13B

SENSING SYSTEM FOR RESPIRATOR

CROSS REFERENCE TO RELATED APPLICATIONS

This application is a national stage filing under 35 U.S.C. 371 of PCT/IB2018/056560, filed Aug. 28, 2018, which claims the benefit of U.S. Provisional Application No. 62/553,569, filed Sep. 1, 2017, the disclosure of which is incorporated by reference in its entirety herein.

BACKGROUND

Particulate matter (PM) sensors are sensing elements that are configured to enable quantification of the concentration of solid particles in an environment, most commonly an environment where particles are suspended in a gas phase. PM sensors have received an increase in attention over the last decade as a result of increased awareness of the possible impact of PM on human health. PM sensors are commonly used to enable environmental PM monitoring, diesel engine soot particle output, and particle filter efficiency measurements, including respirator fit testing. Most of the sensor systems fall into one of the following categories: 1) mass based measurements, which monitor the mass of particles deposited over time by use of a mass balance or quartz crystal microbalance (typically used in environmental monitoring), 2) optical based measurements, where an optical signal is used to monitor the concentration of particles in an airstream (typically used in environmental monitoring and quantitative respirator fit testing), and 3) electrical conductivity sensing, where the deposition of electrically conductive particles on a pair of electrodes results in a measureable electrical signal (typically used in diesel engine soot monitoring, because soot particles are electrically conductive).

Mass based measurements are generally cumbersome, or require relatively expensive quartz crystal elements and frequency counting electronics. Optical sensing also requires relatively expensive optical systems and high-power requirements. Electrical property sensors can be made inexpensively, because in their most simplistic form can consist only of a pair of electrodes on a substrate. However, existing PM sensors based on electrical property measurements, such as those employed in diesel engine soot sensing, require that the particles of interest be conductive in their solid state. This requirement precludes the sensors from being used to monitor solid particles which are electrically insulating, such as solid salt particles. Additionally, electrical property sensors can be affected by changes in environmental conditions, such as temperature and humidity changes.

SUMMARY

The present disclosure relates to a sensing system of a respirator. In particular, this disclosure relates to an electronic sensing system configured to wirelessly communicate with a reader a change in an electrical property (resistance, capacitance, or other AC impedance properties) of a sensor positioned substantially within an interior gas space of the respirator.

In one aspect, a system includes a respirator, a sensor including a sensing element, and a reader configured to be in wireless communication with the sensor. The sensor is positioned substantially within an interior gas space of the respirator.

The above summary is not intended to describe each embodiment or every implementation of the present disclosure. A more complete understanding will become apparent and appreciated by referring to the following detailed description and claims taken in conjunction with the accompanying drawings. In other words, these and various other features and advantages will be apparent from a reading of the following detailed description.

BRIEF DESCRIPTION OF THE DRAWINGS

Figure 13B:
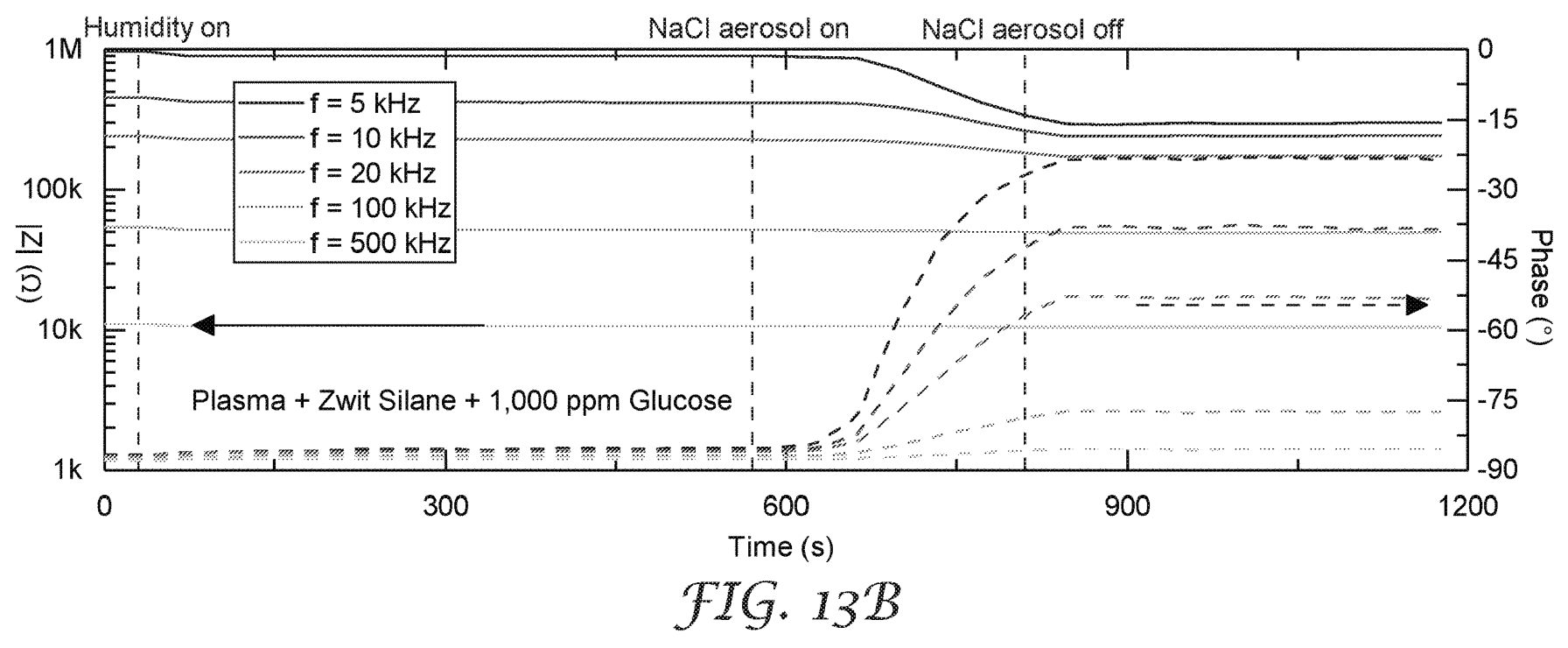

FIG. 13A-13D are graphs that illustrate a comparison of isothermal water uptake and NaCl aerosol response for O2+TMS plasma+zwitterionic silane followed by different coat weights of glucose applied to salt aerosol sensor.

DETAILED DESCRIPTION

Figure 1:
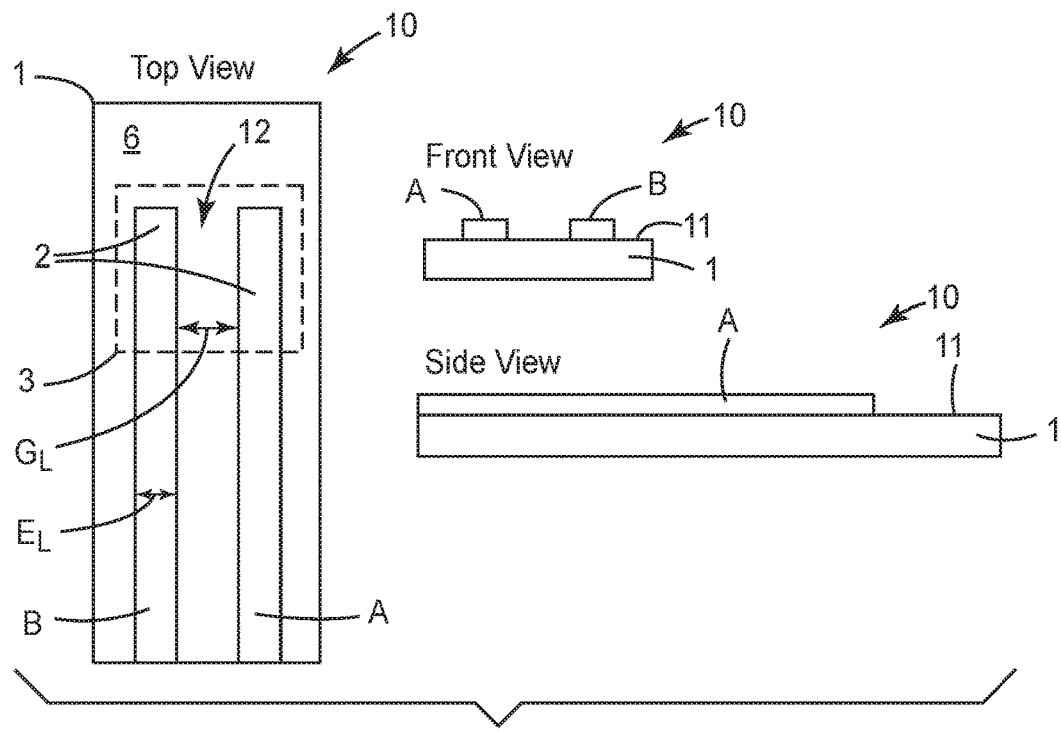
FIG. 1 is a schematic diagram of top, front and side view of an illustrative sensing element.
Figure 2:
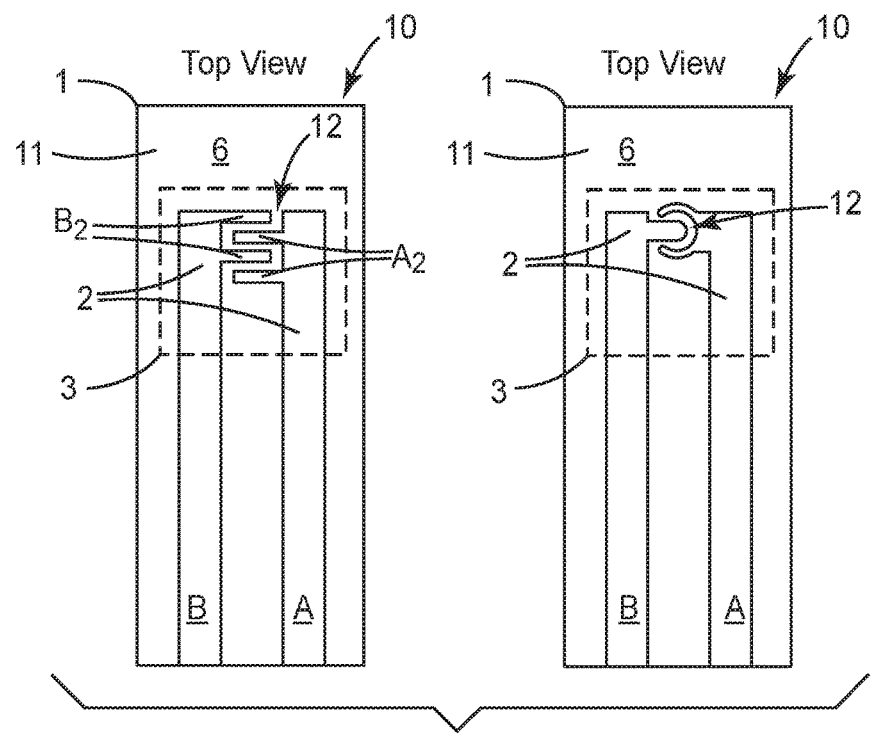
FIG. 2 are schematic diagrams of top views of two illustrative sensing elements.

In the following detailed description, reference is made to the accompanying drawings that form a part hereof, and in which are shown by way of illustration several specific embodiments. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open-ended sense, and generally mean "including, but not limited to". It will be understood that "consisting essentially of", "consisting of", and the like are subsumed in "comprising," and the like.

As used herein, the terms "fluid-soluble" and "fluid-ionizable" are equivalent in this disclosure.

The present disclosure relates to a sensing system of a respirator. In particular, this disclosure relates to an electronic sensing system configured to wirelessly communicate with a reader a change in an electrical property (resistance, capacitance, or AC impedance) of a sensor positioned substantially within an interior gas space of the respirator. The system includes a respirator, a sensor including a sensing element, and a reader configured to be in wireless communication with the sensor. The sensor is positioned substantially within an interior gas space of the respirator. The electronic sensing element may be configured to enable compensation of background noise induced by environmental factors, for example, temperature, humidity, and gaseous component interactions. The electronic sensing element may also be configured to be easily plugged into and removed from a sensor to enable readout of the sensing element signal. In some cases, the sensor may be wireless, enabling a completely wireless aerosol monitoring system, with disposable sensor elements, that may be configured to be integrated with a respiratory protection device. The electronic sensing element may enable the electrical detection of some particles which are non-conducting in the solid particle state, and also provides a means of background compensation for environmental changes. The electronic sensing element is configured to detect particles which dissolve into conductive components in a fluid. For example, crystalline salt particles, such as sodium chloride particles, are electrically insulating in the solid particle state, but dissolve into conductive sodium and chloride ions in polar fluids, such as water. The sensing element enables detection of these particles because the surface of the sensing element is designed such that a fluid film forms in the region between the electrodes. When the particles of interest impact the sensing element, they dissolve into the fluid, which then enables detection. The sensing element may be designed such that the fluid film forms from gases in the environment. As an example, the fluid may be formed by the condensation of water vapor from human breath. In this example, the sensing element may be placed inside of a respirator for use in respirator fit testing. Aerosolized salt particles which leak into the respirator may impact the sensing element surface, which has a fluid layer formed by the water vapor in the exhaled breath of the wearer, to enable leak detection of the respirator.

Background compensation may be provided by a second pair of electrodes on the sensing element surface (although the two pairs of electrodes may share a single common ground element). This second pair of electrodes, the reference electrodes, may have a particle filtering element above the surface of the electrode which may prevent the particles of interest from interacting with the reference electrode. However, with appropriate pressure drop of the filtering element, the same gaseous components which interact with the first pair of electrodes may be able to pass through the filter and also interact with the second pair of reference electrodes. The surface modification surrounding the electrode pairs may be patterned such that there is a discontinuity in the fluid between the electrode pairs. This discontinuity may prevent the migration of elements from one electrode pair to the other. This assembly results in a reference electrode pair which experiences the environmental effects experienced by the first electrode pair, but a lesser amount of the particulate effects. This enables a way of removing the environmental effects from the signal recorded by the first pair of electrodes. In some embodiments, the reference electrode pair may have the particulate material of interest predisposed on the surface, such that the background compensation signal includes the environmental interaction with the PM of interest. For example, if the sensing element is configured to monitor sodium chloride particles, the reference pair may be pre-loaded with a known amount of sodium chloride, so that when the signal from the first pair of electrodes matches the signal from the reference pair, it can be inferred that the first pair of electrodes has the same quantity of sodium chloride as the reference pair. While the present disclosure is not so limited, an appreciation of various aspects of the disclosure will be gained through a discussion of the examples provided below.

FIG. 1 is a schematic diagram of top, front and side view of an illustrative sensing element 10. The sensing element 10 is configured to interact with an environment of interest. The sensing element 10 includes a substrate 1 having an electrically non-conductive surface 11, at least one high surface energy region 3, and an electrode pair structure 2 disposed on the electrically non-conductive surface 11. The electrode pair structure 2 includes at least one pair of electrodes A, B having a gap 12 therebetween. At least one of the electrodes A or B is at least partially within the at least one high surface energy region 3. The sensing element 10 is configured to sense fluid-soluble particulate matter.

At least some of the high surface energy region 3 may be overlapping and adjacent to the electrode pair structure 2 or the electrode pair A, B, and may be configured to interact with an environment of interest, by, for example, promoting the condensation of gaseous molecules or particulate matter into a condensed fluid on the high surface energy region 3 and particularly within the gap 12 of the electrode pair structure 2 or the electrode pair A, B, or promoting the sensitivity to a component of interest.

Fluid-soluble particulate matter is particulate matter that may, or may not, be electrically conductive in the solid-state form, but may ionize into electrically conductive components in a fluid, such as water. Dissolution of the fluid-soluble particulate matter in the fluid may provide a change in an electrical property of the liquid that may be detected or sensed by the electrode pair structure 2. One useful fluid-soluble particulate matter is sodium chloride (NaCl).

The electrodes A and B in the at least one pair of electrodes A, B may be co-planar with respect to each other. The electrodes A and B in the at least one pair of electrodes A, B may be parallel extending or interdigitated, or have any other useful configuration. The gap 12 defined by a distance between the electrodes A and B in the at least one pair of electrodes A, B may have a lateral distance $G_L$ value of any useful value. This lateral distance $G_L$ value may be in a range from 25 to 125 micrometers. The electrodes may have any useful lateral width $E_L$ value. This lateral width $E_L$ value may be in a range from 25 to 125 micrometers. The electrodes A and B may be formed of any electrically conducting and corrosion or oxidation resistant material such as various metals or metal alloys.

The high surface energy region 3 may be patterned onto the substrate 1 or electrically non-conductive surface 11 to provide for selective deposition of liquid onto the substrate 1 or electrically non-conductive surface 11 for contacting the electrode pair structure 2. The high surface energy region 3 may be at least partially, or completely surrounded or circumscribed by one or more low surface energy regions 6. The high surface energy region 3 may provide for selective deposition of liquid or water to form a liquid layer or liquid volume within the gap 12 of the electrode pair structure 2 onto the high surface energy region 3. Thus, the liquid layer or liquid volume may contact both electrodes A and B in the electrode pair structure 2. The high surface energy region 3 may define any useful shape or surface area.

The phrase "high surface energy region" refers to a surface region that exhibits an advancing water contact angle of less than 90 degrees, or less than 80 degrees, or less than 60 degrees, and/or preferably less than 45 degrees, as measured per ASTM D7334-08. It is noted that a water volume of 20 microliters, which is a general recommendation in ASTM D7334-08, may be too large for proper testing depending on the surface geometry. It is necessary that the water volume is small enough in relation to the size of the surface region such that the advancing contact angle is not disturbed by the confinement of the region.

The phrase "low surface energy region" refers to a region with lower surface energy than the high surface energy region, such that the low surface energy region has an advancing water contact angle that is greater than that of the high surface energy region. The low surface energy region may have an advancing water contact angle that is 1-10 degrees, or 10-20 degrees, or 20-45 degrees, and/or preferably more than 45 degrees, greater than that of the high surface energy region.

For example, the high surface energy region 3 may have an advancing water contact angle of 20 degrees, and the low surface energy region 6 may have an advancing water contact angle of 60 degrees. In another example, the high surface energy region 3 may have an advancing water contact angle of 70 degrees, and the low surface energy region 6 may have an advancing water contact angle of 100 degrees. The difference in advancing water contact angles promotes confinement of a condensed fluid to the predefined regions, which may minimize undesirable interactions. The advancing water contact angle may be impacted by the hydrophilic nature of the surface region, or the hygroscopic nature of materials in the surface region which effectively alter the advancing water contact angle.

The high surface energy region 3 may be formed by surface treatment of the substrate 1 or electrically non-conductive surface 11. These surface treatments include, for example, plasma, chemical modification, and the like. Plasma treatments may include oxygen plasma treatment. Chemical treatment includes deposition or vapor deposition of silanes or siloxanes to form, for example, a siloxane surface or a zwitterionic siloxane surface defining the high surface energy region 3. Chemical treatment may also, or alternatively, include deposition of hygroscopic materials to define the high surface energy region 3. The high surface energy region 3 may have a dissolvable ion content of less than 1E-9 moles/mm$^2$. For example, a 1 mm$^2$ surface region with 10 ng of sodium chloride has a dissolvable ion content of approximately 3.45E-10 moles/mm$^2$ (1.72E-10 moles/mm$^2$ contributed by sodium and 1.72E-10 moles/mm$^2$ contributed by chloride) due to the potential dissociation of the sodium chloride into sodium and chloride ions when water condenses on the region. The dissolvable ion content impacts the surface resistivity of the sensor. However, the surface resistivity is also impacted by the ambient environment, such as the relative humidity, due to the varied interactions of the high surface energy region 3 with the environment. For example, for the case of a 1 mm$^2$ surface region with 10 ng of sodium chloride, the surface resistivity will be large in low humidity environments in which the sodium chloride remains a crystalline solid, and the surface resistivity will be lower in high humidity environments in which the sodium chloride absorbs moisture from the air and dissolves into a liquid solution. The dissolvable ion content is also impacted by the ionic dissociation constant of the species in the high surface energy region. For example, sodium chloride has a large ionic dissociation constant in water, while the ionic dissociation constant of a compound such as glucose is much lower. As a result, for an equivalent molar amount of glucose loaded on a surface, the dissolvable ion content of the glucose surface will be significantly lower than that of a surface with sodium chloride.

Hygroscopic materials include materials which absorb or adsorb water from the surrounding environment, and preferably those which absorb or adsorb water vapor from the surrounding gaseous medium. For example, the hygroscopic material may be a salt, an acid, a base, or preferably a compound with a low ionic dissociation constant in water such as a water-absorbing polymer, a monosaccharide, a polysaccharide, an alcohol, or more preferably a polyol, such that the surface resistivity change of the sensor due to absorption or adsorption of water is minimized.

The polyol may be a polymeric polyol or a monomeric polyol and may preferably be a sugar alcohol, such as sorbitol. The hygroscopic layer is preferably a compound which enhances water retention and may also be within the class of compounds known as humectants. The hygroscopic material is preferably a material which has a deliquescence point of less than 100 percent relative humidity, or less than 90 percent relative humidity, or more preferably less than 80 percent relative humidity at 25 degrees Celsius and 1 atmosphere of pressure. The deliquescence point is taken to refer to the relative humidity at which the material absorbs enough water from the surrounding gaseous medium such that it dissolves and forms a liquid solution. The formation of the liquid solution may enhance the performance of the fluid ionizable particulate matter sensing element by providing a liquid solution that a particle may dissolve into. The hygroscopic material and coating weight are preferably chosen such that the electronic mobility of the ions of the dissolved particulate matter of interest is minimally decreased by the effects of the hygroscopic material.

The substrate 1 may be formed of any electrically non-conductive material. The substrate 1 may be a laminate or a single material construction. The substrate 1 may be formed of any material used as circuit board or electrical sensor substrates. The substrate 1 may be formed of any glass or dielectric resin. Illustrative substrate 1 material is commercially available from Advanced Circuits, Colorado, USA, among other printed circuit board fabrication entities.

FIG. 2 are schematic diagrams of top views of illustrative sensing elements 10. The sensing element 10 includes a substrate 1 comprising an electrically non-conductive surface 11, at least one high surface energy region 3, and an electrode pair structure 2 disposed on the electrically non-conductive surface 11, as described above. The electrode pair structure 2 includes at least one pair of electrodes A, B having a gap 12 therebetween. At least one of the electrodes A or B is at least partially within the at least one high surface energy region 3, as described above. The sensing element 10 is configured to sense fluid-soluble particulate matter.

FIG. 2 on the left illustrates an interdigitated electrode pair A, B having two opposing pairs of interdigitated members $A_2$ and $B_2$. The gap 12 between interdigitated members $A_2$ and $B_2$ may have a lateral distance value of any useful value. This distance value may be in a range from 25 to 125 micrometers. The interdigitated members $A_2$ and $B_2$ may have any useful lateral width. This lateral width may be in a range from 25 to 125 micrometers. The interdigitated members $A_2$ and $B_2$ may have any useful length such as a range from 500 to 10,000 micrometers. The interdigitated members $A_2$ and $B_2$ may be formed of any electrically conducting and corrosion or oxidation resistant material such as various metals or metal alloys. The interdigitated electrode pair A, B is shown with four interdigitated members however the interdigitated electrode pair A, B may have any number of total interdigitated members, such as in a range from 2 to 50, or 4 to 40.

FIG. 2 on the right illustrates another embodiment of the sensing element 10 where the electrode pair structure 2 defines a first electrode B at least partially surrounding a second electrode A and defining a gap 12 therebetween.

FIG. 3 is a schematic diagram cross-sectional view of one illustrative sensing element 10. FIG. 3 provides an illustration of a suitable layering structure that can be applied to the electrically non-conductive surface 11 and electrode pair structure 2 to define the high surface energy region 3 and enhance the electrical impedance response to a fluid soluble target particulate material such as a salt aerosol, for example. The electrode pair structure 2 includes at least one pair of electrodes A, B having a gap 12 therebetween.

An illustrative surface treatment layer 120 may include a zwitterionic silane layer or surface chemically grafted to a siloxane layer or surface (where the siloxane surface may be formed by an oxygen+tetramethyl silane plasma treatment as illustrated in FIG. 5A). This illustrative surface treatment layer 120 may be referred to as a silane surface treatment layer 120. This illustrative surface treatment layer 120 may exist predominantly on the surface of the electrically non-conductive surface 11 in between electrode pair structure 2 or between at least one pair of electrodes A, B or within the gap 12. The illustrative surface treatment layer 120 may define the high surface energy region 3.

FIG. 5A is a flow diagram of a process for forming the illustrative surface treatment layer 120. This process includes forming electrodes A, B on the electrically non-conductive surface 11 at step 210. Then a masking layer is applied to define the high surface energy region on the the electrically non-conductive surface 11 at step 220, such that at least one electrode A or B is at least partially within the defined high surface energy region. The masking layer may be applied to the electrically non-conductive surface 11, such that some region of the electrically non-conductive surface 11 is exposed to the subsequent treatments, and some regions are protected from the subsequent treatments. The regions protected from subsequent treatments may form low surface energy regions. A suitable masking layer is any layer that forms a desired pattern for forming the desired surface composition and may resist plasma treatment in defined locations. For example, a suitable masking layer is a tape commercially available under the trade designation "3M Vinyl Tape 491" from 3M, MN, USA.

The masked article is placed in a vacuum chamber at step 230. The vacuum chamber may provide a vacuum environment of 100 mTorr or less, or 50 mTorr or less. Then an oxygen plasma is applied to the masked article at step 231. Oxygen gas (for example, at a concentration of 500 parts per million (ppm)) may be introduced and formed into a plasma in fluid contact with at least some of the electrode surface for a period of time (for example, sixty seconds). In certain embodiments, the plasma may be generated by applying a 500 W radiofrequency field. Then a silane is deposited or vapor deposited onto the plasma treated article at step 232. Tetramethyl silane (for example, at a concentration of 150 ppm) may then be added to the plasma for a period of time (for example, thirty seconds). The tetramethylsilane flow may be interrupted, and oxygen plasma continues for a period of time (for example, sixty seconds). The second oxygen plasma is applied to the masked article at step 233. Then the plasma treated article is removed from the vacuum chamber at step 234.

Then a zwitterionic silane solution is coated onto the treated article at step 240. The solution containing a zwitterionic silane, for example at 2 wt % in water, is applied in fluid contact with the sensing element surface for a period of time (for example, ten seconds). The coated article is blown dry at step 241 and then baked at an elevated temperature for a period of time (for example, ten minutes at 110° C.). The sensing element 10 is then rinsed at step 250 with deionized water and dried at step 251.

The silane surface treatment layer 120 may be formed of compounds having formula (I) as described in International Patent Publication No. WO2016/044082A1 (Riddle, et al.):

$$(R^1O)_p—Si(Q^1)_q\text{-}W—N^+(R_2)(R_3)—(CH_2)_m—Z^{t-} \quad \text{(I)}$$

wherein:

each $R^1$ is independently a hydrogen, methyl group, or ethyl group;

each $Q^1$ is independently selected from hydroxyl, alkyl groups containing from 1 to 4 carbon atoms, and alkoxy groups containing from 1 to 4 carbon atoms;

each $R^2$ and $R^3$ is independently a saturated or unsaturated, straight chain, branched, or cyclic organic group (preferably having 20 carbons or less), which may be joined together, optionally with atoms of the group W, to form a ring;

W is an organic linking group;

$Z^{t-}$ is $-SO_3^-$, $-CO_2^-$, $-OPO_3^{2-}$, $-PO_3^{2-}$, $-OP(=O)(R)O^-$, or a combination thereof, wherein t is 1 or 2, and R is an aliphatic, aromatic, branched, linear, cyclic, or heterocyclic group (preferably having 20 carbons or less, more preferably R is aliphatic having 20 carbons or less, and even more preferably R is methyl, ethyl, propyl, or butyl);

p is an integer of 1 to 3;

m is an integer of 1 to 11;

q is 0 or 1; and p+q=3.

Suitable examples of zwitterionic silane compounds of Formula (I) are described in U.S. Pat. No. 5,936,703 (Miyazaki et al.), including, for example:

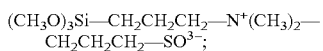
$(CH_3O)_3Si-CH_2CH_2CH_2-N^+(CH_3)_2-CH_2CH_2CH_2-SO^{3-}$;

and

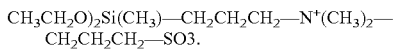
$CH_3CH_2O)_2Si(CH_3)-CH_2CH_2CH_2-N^+(CH_3)_2-CH_2CH_2CH_2-SO3$.

Other examples of suitable zwitterionic silane compounds and their preparation are described in U.S. patent application Ser. No. 13/806,056 (Gustafson et al.), including, for example:

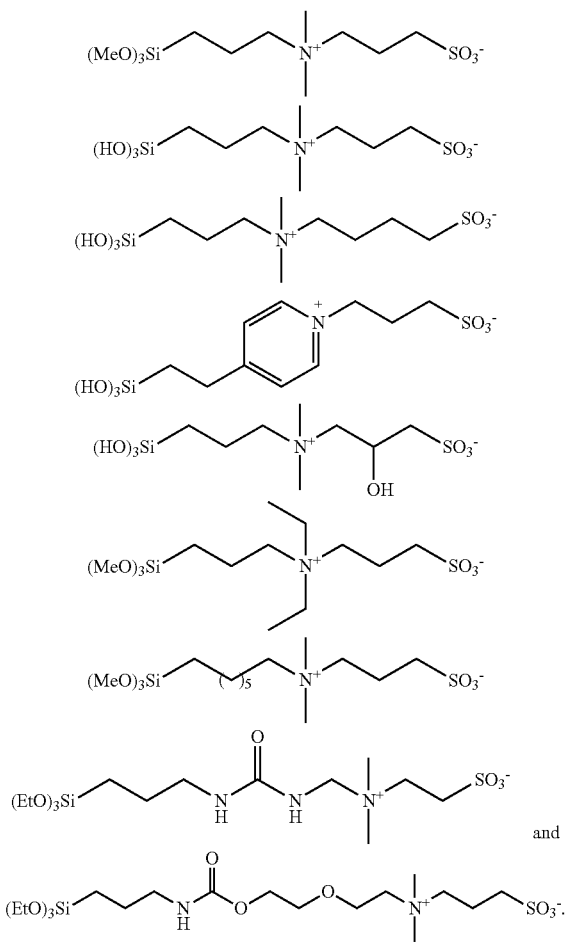

In some embodiments, a layer of salt material 140 is applied to the sensing element 10 or surface treatment layer 120 of the sensing element 10. The layer of salt material 140 may provide for a reference electrical property value of the electrode pair A, B. This may be useful when two or more electrode pairs are utilized with the sensing element 10. The layer of salt material 140 may be disposed on the high surface energy region 3.

In some embodiments, a layer 130 comprising a hygroscopic material may be applied to the sensing element 10 or surface treatment layer 120 of the sensing element 10, and then allowed to dry. In some of these embodiments, a layer of salt material 140 may be disposed on or with the hygroscopic material layer 130 within the high surface energy region 3 of the sensing element 10. The salt material 140 may mix with the hygroscopic material layer 130 to form a combined hygroscopic material and salt layer 130, 140.

Figure 5A:
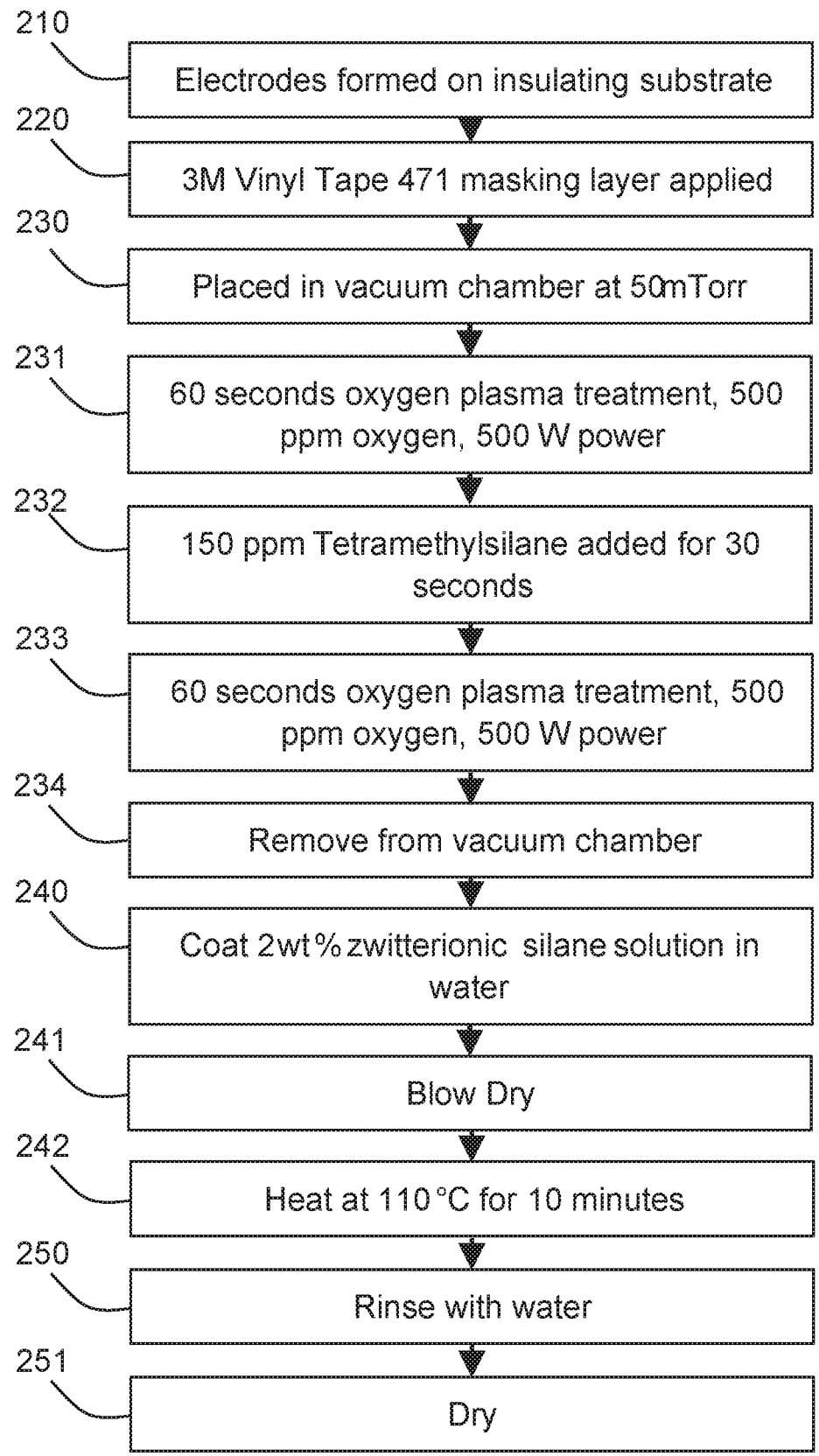
FIG. 5A is a flow diagram of an illustrative method of making a sensing element.
Figure 5B:
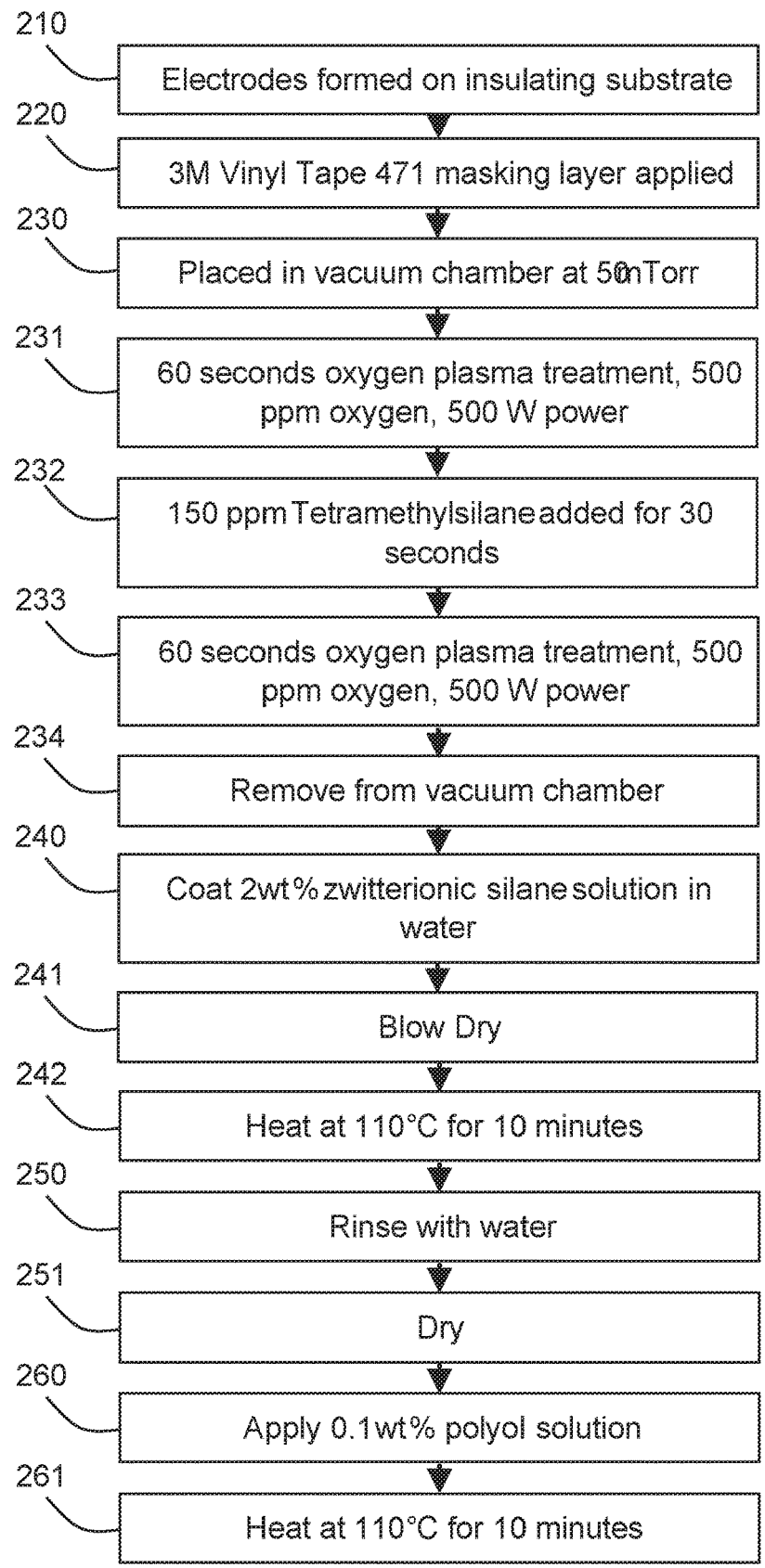
FIG. 5B is a flow diagram of another illustrative method of making a sensing element.

In some embodiments, a hygroscopic material layer 130 is disposed on the sensing element 10 and is in contact with at least one of layers 11, 120 and electrode pair structure 2. FIG. 5B is a flow diagram of the process of FIG. 5A described above with the addition of the hygroscopic material layer 130. The sensing element 10 with the surface treatment layer 120 of FIG. 5A is then treated with a hygroscopic material solution (for example, a hygroscopic material solution may be 0.1 wt % sorbitol in water) at step 260 and heated to 110 degrees Celsius at step 261. This illustrative hygroscopic material layer 130 may exist predominantly on the surface of the electrically non-conductive surface 11 in between electrode pair structure 2 or between at least one pair of electrodes A, B or within the gap 12 or on the surface treatment layer 120. The illustrative surface treatment layer 130 may define the high surface energy region 3.

In some embodiments, the addition of a hygroscopic material layer 130 may be used to modify the hygroscopic properties of a sensing element 10 surface to which it is applied and may define the high surface energy region 3 on the sensing element 10. When used on a surface of a sensing element 10 that functions based on electrical impedance variations, some hygroscopic materials have the property of altering hygroscopic properties without contributing mobile ions in solution. Additionally, some hygroscopic materials have another advantageous property of low vapor pressure. The hygroscopic properties of polyols are due to their water activity, which is influenced by presence of a large number of hydroxyl groups in the molecule. The water activity thermodynamics of a variety of polyol sugar alcohols are described by Compernolle, S. and Muller, J.-F., Atmos. Chem. Phys., 14, 12815-12837 (2014). For example, sorbitol is shown to form a thermodynamically stable water-sorbitol mixture at relative humidity greater than 40%. This property may be advantageous when the sensing element 10 to be modified functions based on the ionization of particles in a liquid. The presence of a hygroscopic material, such as a sugar alcohol, on the sensing element 10 or surface of the electrically non-conductive surface 11 in between electrode pair structure 2 or between at least one pair of electrodes A, B or within the gap 12 or on the surface treatment layer 120 may enable use in a wider range of humidity environments.

In certain embodiments, the hygroscopic material layer 130 includes compounds with a plurality of hydroxyl groups. For example, the hygroscopic material layer 130 may be comprised of polyethylene glycol available from Sigma-Aldrich, MO, USA. In other suitable examples, the polyol layer may include at least one sugar alcohol. Some examples of suitable sugar alcohols include glycerol, erythritol, arabitol, xylitol, ribitol, mannitol, sorbitol, galactitol, allitol, iditol, maltitol, isomalitol, lactitol, dulcitol, and talito, all available from Sigma-Aldrich, MO, USA. In other suitable examples, the polyol layer 130 may include saccharide compounds. Some examples of suitable saccharides include glucose, fructose, galactose, sucrose, lactose, cellulose and starch available from Sigma-Aldrich, MO, USA.

The thickness of the surface treatment layer 120 or the silane surface treatment layer 120 may be any useful thickness. In many embodiments, the surface treatment layer 120 or the silane surface treatment layer 120 is less than 50 nanometers, or from 1 to 50 nanometers thick.

When present, the thickness of the hygroscopic material layer 130 may be any useful thickness. In some embodiments, the thickness of the hygroscopic material layer 130 may be from 0.1 to 10 micrometers thick. Thicknesses greater than 10 micrometers or less than 0.1 micrometers may be useful also. The thickness of the hygroscopic material layer 130 may impact the total amount of water absorption, as well as the kinetics of absorption. By altering the thickness, which may be accomplished by altering the coating weight, the sensing element response may be improved for a given environment. Examples of the impact of the hygroscopic layer thickness is illustrated in FIG. 13A-13D.

The sensing element 10 may omit one or more of the layers described above, and the layers may be constructed with a range of coating weights and thickness combinations, as desired. When used with a sensing element 10 that functions based on electrical impedance variations, the silane surface treatment layer 120 has the property of altering surface properties without contributing significant amounts of mobile ions in solution. In some embodiments, the addition of a hygroscopic material layer 130 may be used to modify the hygroscopic properties of sensing element 10 and assist in defining the high surface energy region 3 on the sensing element 10. When used with a sensing element 10 that functions based on electrical impedance variations, the hygroscopic material layer 130 may have the property of altering surface properties without contributing significant amounts of mobile ions in solution.

Figure 4A:
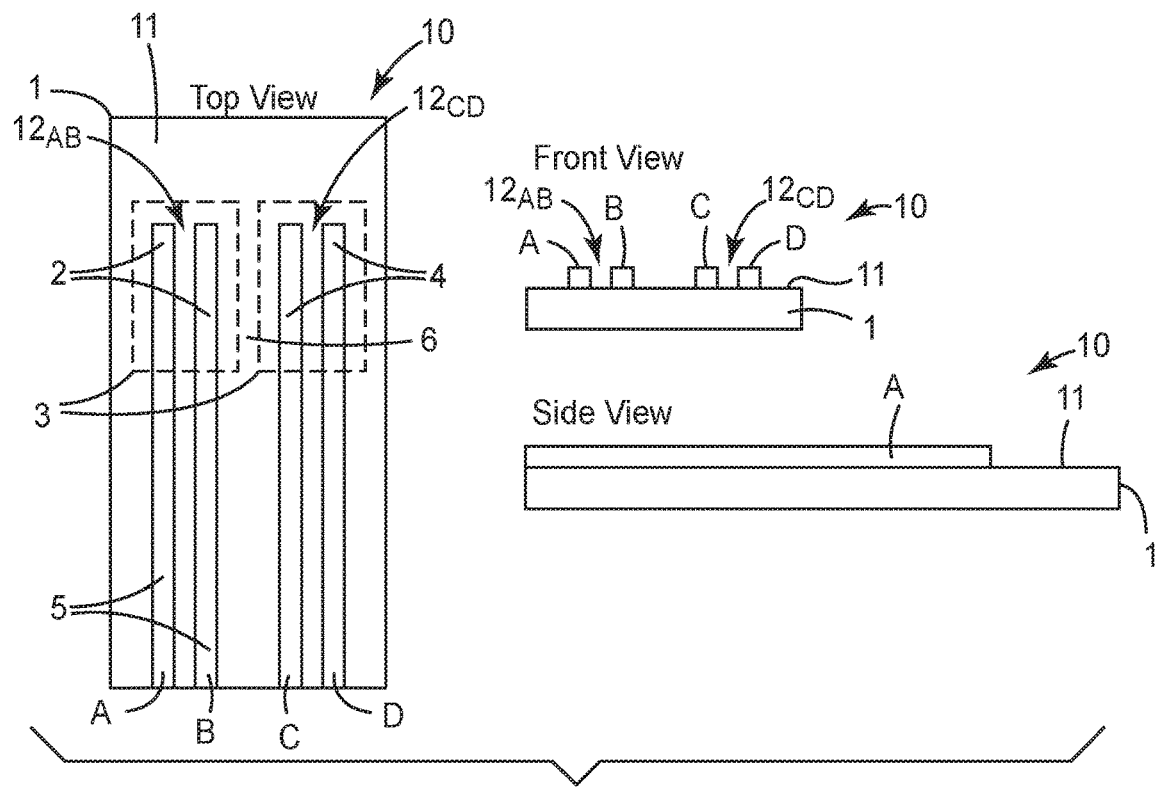
FIG. 4A is a schematic diagram of top, front and side view of another illustrative sensing element.

FIG. 4A is a schematic diagram of top, front, and side view of another illustrative sensing element 10 having two electrode pair structures 2, 4, or two pairs of electrodes A, B and C, D.

The sensing element 10 is configured to interact with an environment of interest. The sensing element 10 includes a substrate 1 including an electrically non-conductive surface 11, two high surface energy regions 3, and two electrode pair structures 2, 4 disposed on the electrically non-conductive surface 11. Each electrode pair structure 2, 4 includes at least one pair of electrodes A, B and C, D having a gap $12_{AB}$ and $12_{CD}$ therebetween. At least a portion of each electrode pair structure 2, 4 is within the corresponding high surface energy region 3. The high surface energy region 3 may be discontinuous, such that a lower surface energy region 6 separates the high surface energy region 3 corresponding to each electrode pair A, B and C, D, as illustrated. The sensing element 10 is configured to sense fluid-soluble or fluid-ionizable particulate matter. A low surface energy region 6 may separate the two high surface energy regions 3. A conductive region 5 may electrically connect the electrode pair structure 2, 4 with sensing electronics. This electrode configuration may be referred to as including four electrodes A, B, C, and D where two pairs of electrodes are formed A-B and C-D.

The low surface energy region 6 may assist in keeping liquid in each of the two high surface energy regions 3 separate from each other. Regions outside of the perimeter of the high surface energy regions 3 may have a lower surface energy than the surface energy within the perimeter of the high surface energy regions 3. Thus, liquid vapor or water vapor may selectively condense and form a liquid layer or liquid volume that remain within the perimeter of the high surface energy regions 3.

Water vapor may be produced by human breath inside of a respirator, such as a filtering facepiece respirator (FFR) or elastomeric respirator, for example. This water vapor may condense onto the high surface energy region 3 of the sensing element. In an example, salt aerosol particles, such as sodium chloride, may come into contact with this condensed water vapor so that the salt particle dissolves and alters an electrical property (for example, impedance) of at least one of the electrode pairs A, B and C, D. The spatially separated surface treatments enable distinctly separate signals by preventing molecular migration between the electrode pair structures 2 and 4.

Figure 3:
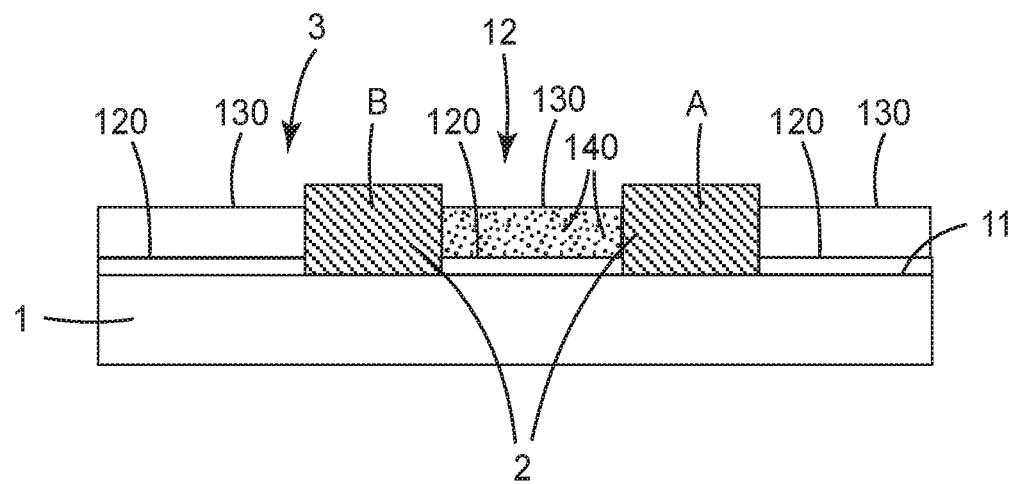
FIG. 3 is a schematic diagram cross-sectional view of an illustrative sensing element.

In some embodiments, at least a portion of a region surrounding at least one of the electrode pair structures 2, 4 may have a particulate or salt material predisposed on the electrode pair structures 2, 4 or within the gap $12_{AB}$, $12_{CD}$ therebetween (as illustrated in FIG. 3). For example, sodium chloride may be predisposed on a surface surrounding an electrode pair structure 2 or 4 or within the gap $12_{AB}$ or $12_{CD}$ to generate an electrical impedance related to the quantity of predisposed sodium chloride. This may be referred to as a reference electrode. The solid material (sodium chloride, for example) may be disposed or provided within the perimeter of one high surface energy region 3 in a known amount. Once water vapor condenses on this high surface energy region 3 the known amount of solid material (sodium chloride, for example) is dissolved and may provide a reference electrical property or reference electrode (electrode pair structure 2 or 4) that a sensing electrode (remaining electrode of 2 or 4) may be compared to during testing or the sensing operation.

Figure 4B:
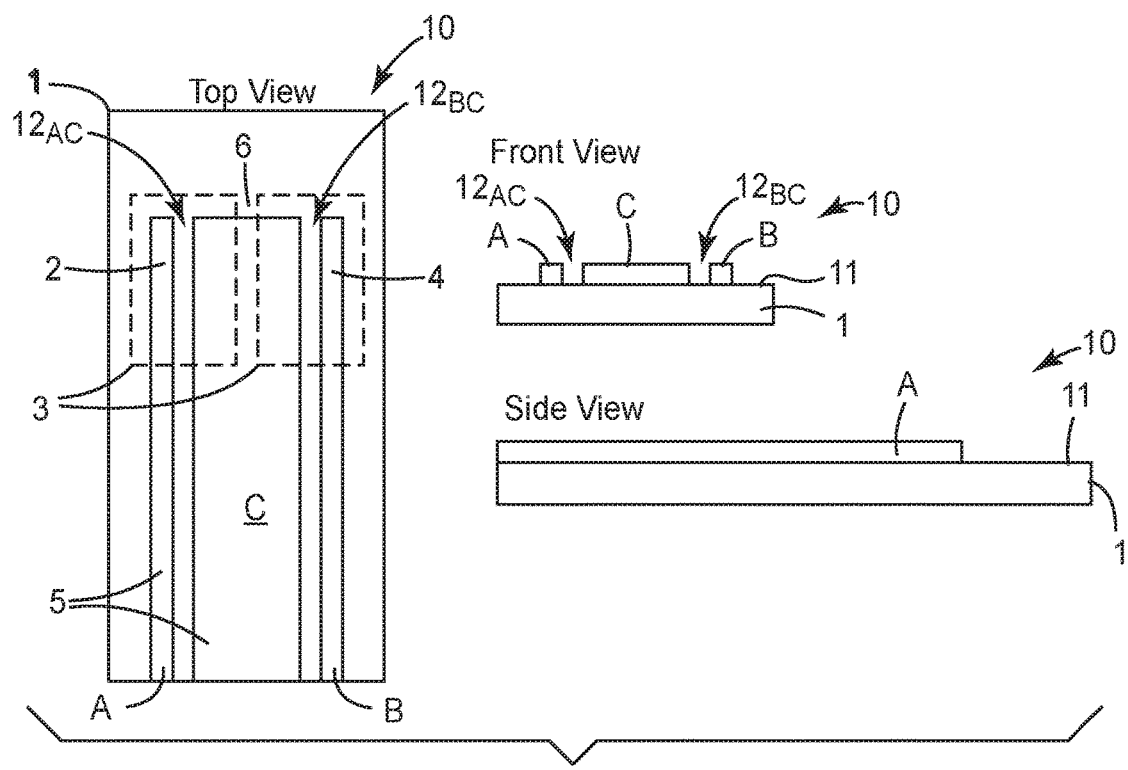
FIG. 4B is a schematic diagram of top, front and side view of another illustrative sensing element.

FIG. 4B is a schematic diagram of top, front, and side view of another illustrative sensing element 10.

The sensing element 10 is configured to interact with an environment of interest. The sensing element 10 includes a substrate 1 comprising an electrically non-conductive surface 11, two high surface energy regions 3, and two electrode pair structures 2, 4 disposed on the electrically non-conductive surface 11. Each electrode pair structure 2, 4 includes one electrode and share a common electrode C and having a gap $12_{AC}$, $12_{BC}$ therebetween. At least a portion of each electrode pair structure 2, 4 is within the corresponding high surface energy region 3. The sensing element 10 is configured to sense fluid-soluble particulate matter. A low surface energy region 6 may separate the two high surface energy regions 3. A conductive region 5 may electrically connect the electrode pair structure 2, 4 with sensing electronics. This electrode configuration may be referred to as comprising three electrodes A, B, and C where two pairs of electrodes are formed A-C and B-C and where electrode C is common to both electrode pairs.

The sensing element may be configured to be electrically coupled or decoupled to one or more additional electronic elements by a physical proximity to one or more electronic elements. In some embodiments, for example, an electrically conducting region 5 may be configured for physical contact with an electronic element in a connector. In some embodiments, for example, an electrically conducting region 5 may be configured to electrically couple with another electronic element without physical contact via a time-varying electromagnetic field.

Figure 6:
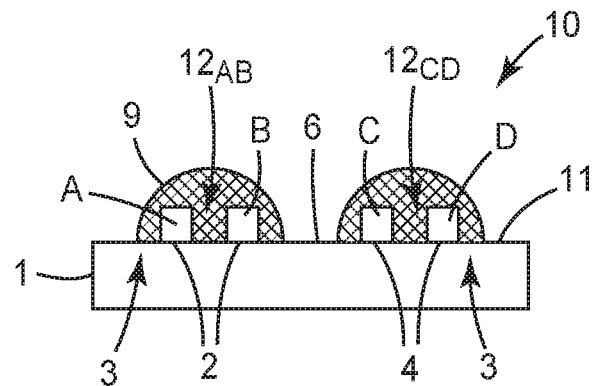
FIG. 6 is a schematic diagram cross-sectional view of the sensing element of FIG. 4A illustrating fluid disposed on the electrode pair structures.

FIG. 6 is a schematic diagram cross-sectional view of the sensing element 10 of FIG. 4A illustrating fluid 9 disposed on the electrode pair structures 2, 4. The sensing element 10 includes a substrate 1 including an electrically non-conductive surface 11, two high surface energy regions 3, and two electrode pair structures 2, 4 disposed on the electrically non-conductive surface 11. Each electrode pair structure 2, 4 includes at least one pair of electrodes A, B, and C, D having a gap $12_{AB}$ and $12_{CD}$ therebetween. At least a portion of each electrode pair structure 2, 4 is within the corresponding high surface energy region 3. The sensing element 10 is configured to sense fluid-soluble particulate matter. A low surface energy region 6 may separate the two high surface energy regions 3. The configuration of the high surface energy regions 3 enables the selective condensation of water or liquid vapor onto these high surface energy regions 3 to form the liquid bubbles, or liquid layers, or liquid volumes 9.

In embodiments with multiple electrode pairs A, B, and C, D, the regions of different surface energies may be configured such that fluid 9, as illustrated in an example in FIG. 6, preferentially wets the high surface energy regions 3 surrounding at least one of the electrode pairs A, B, or C, D, but the fluid 9 does not make fluid contact with the other electrode pair A, B, or C, D. The preferential separation of fluid contact with the different electrode pairs is shown in FIG. 6, where fluid 9 preferentially wets the regions proximal to the two electrode pairs 2 and 4, but does not form a fluid bridge between the pairs A, B, and C, D, due to the low surface energy region 6. Liquid or water 9 has a lower affinity to wet region 6, producing multiple distinct fluid regions 9 that are not in fluid communication with one another.

Figure 7:
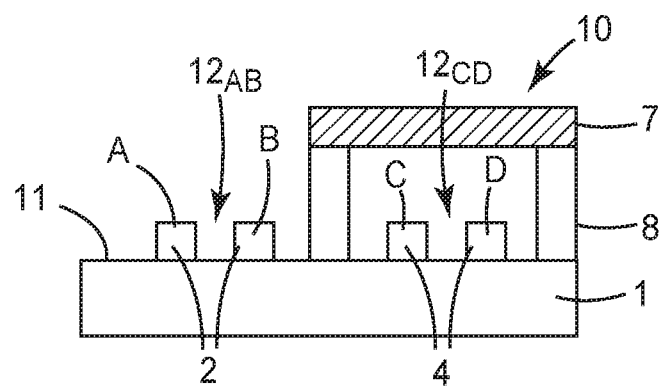
FIG. 7 is a schematic diagram cross-sectional view of an illustrative sensing element with a filtering element.
Figure 8:
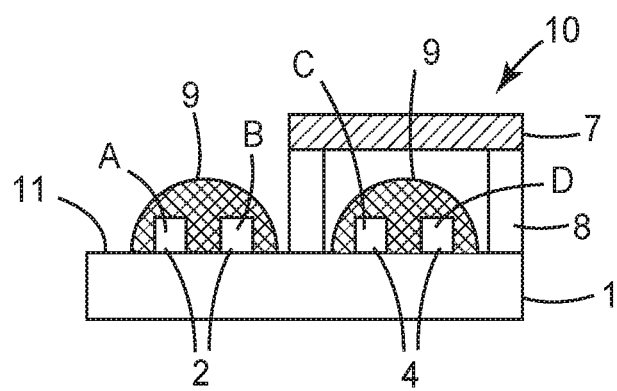
FIG. 8 is a schematic diagram cross-sectional view of the sensing element of FIG. 7 illustrating fluid disposed on the electrode pair structures.

FIG. 7 is a schematic diagram cross-sectional view of an illustrative sensing element 10 with a filtering element 7. FIG. 8 is a schematic diagram cross-sectional view of the sensing element of FIG. 7 illustrating fluid 9 disposed on the electrode pair structures 2, 4.

The filtering element 7 may be configured such that it prevents at least some particles or a component from the environment from contacting at least one electrode pair C, D. In some embodiments, the particulate filter 7 may be a nonwoven filter element. In some embodiments, a standoff material 8 is disposed on the electrically non-conductive surface 11, such that the material 8 surrounds at least a portion of an electrode pair structure 4, and the filter material 7 is disposed on the standoff material 8 such that the filter material 7 is configured to not physically contact the electrode pair C, D.

One suitable example of a standoff material 8 is an adhesive foam commercially available under the trade designation "3M Urethane Foam Tape 4056" from 3M Co., MN, USA, for example. The standoff material 8 or foam may have an ionic content of less than 1000 ppm, such that the extraction of ions by a condensed fluid is minimized. As an example, this configuration may result in a reference electrode pair C, D, that may interact with gaseous compounds in the environment which are able to pass through the filter material 7. However, at least some particles are intercepted by the filter material 7 and are prevented from interacting with the reference electrode pair C, D.

The filtering element 7 may provide the only airflow communication with the electrode pair structure 4 or electrode pair C, D and the surrounding environment, but does not provide particulate communication with the electrode and the surrounding environment. Thus, the electrode pair structure 4 may operate as a real-time reference electrode that may remove environmental effects from the sensing signal of the sensing electrode pair structure 2 or electrode pair A, B (not protected by the filtering element 7), for example. In other embodiments, a fixed amount of solid material of interest, such as salt 140 (see FIG. 3) or sodium chloride, may be disposed on the reference electrode pair structure 4 or electrode pair C, D and contained by the filtering element 7. This configuration may provide a reference electrode pair or electrode pair structure 4 or electrode pair C, D that has a set signal to the sensing electronics for comparison with the sensing electrode pair or structure 2 or electrode pair A, B (not protected by the filtering element 7).

Figure 9:
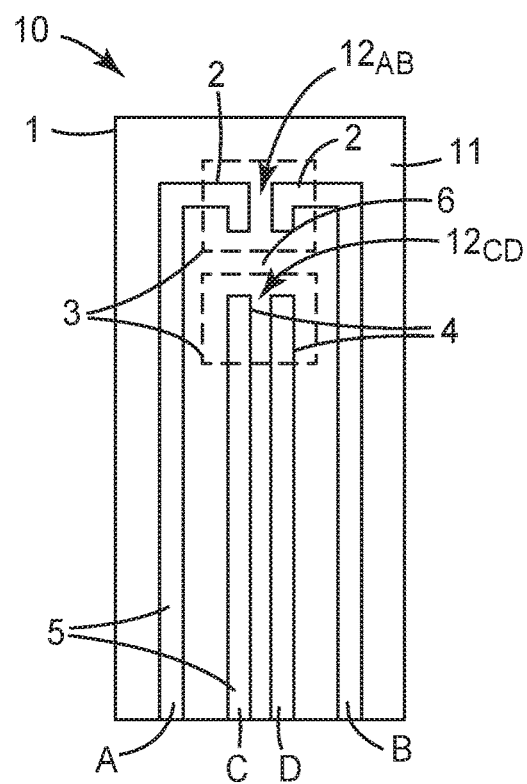
FIG. 9 is a schematic diagram of top view of another illustrative sensing element.

FIG. 9 is a schematic diagram of the top view of another illustrative sensing element 10. The sensing element 10 includes a substrate 1 comprising an electrically non-conductive surface 11, two high surface energy regions 3, and two electrode pair structures 2, 4 disposed on the electrically non-conductive surface 11. Each electrode pair structure 2, 4 includes at least one pair of electrodes A, B and C, D having a gap $12_{AB}$ and $12_{CD}$ therebetween. At least a portion of each electrode pair structure 2, 4 is within the corresponding high surface energy region 3. The sensing element 10 is configured to sense fluid-soluble particulate matter. A low surface energy region 6 may separate the two high surface energy regions 3. Here one electrode pair A, B is between the other electrode pair C, D. The inner electrode pair C, D is shown as linear, parallel and co-extending, however, the inner electrode pair C, D may be interdigitated as described above.

Figure 10:
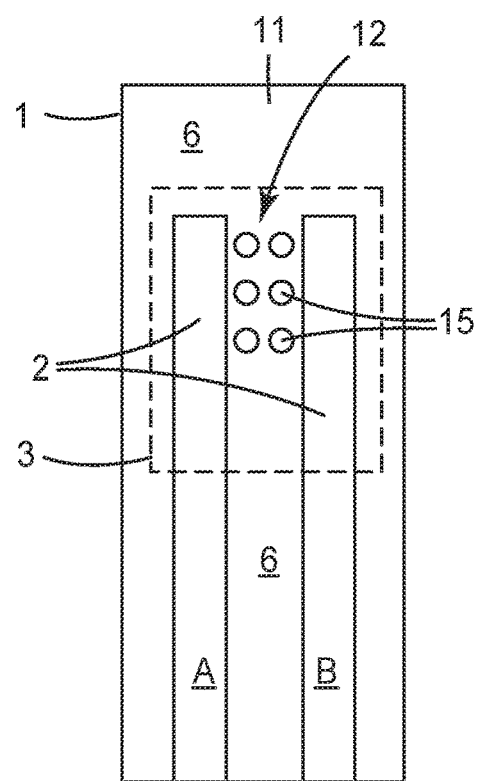
FIG. 10 is a schematic diagram of top view of another illustrative sensing element.

FIG. 10 is a schematic diagram of the top view of another illustrative sensing element 10. The sensing element 10 includes a substrate 1 comprising an electrically non-conductive surface 11, one high surface energy region 3, and one electrode pair structure 2 disposed on the electrically non-conductive surface 11. The electrode pair structure 2 includes at least one pair of electrodes A, B having a gap 12 therebetween. At least a portion of each electrode pair structure 2 is within the high surface energy region 3. The sensing element 10 is configured to sense fluid-soluble particulate matter. A low surface energy region 6 may surround or circumscribe the high surface energy region 3. The electrode pair A, B is shown as linear, parallel and co-extending, however, the electrode pair A, B may be interdigitated as described above. One or more perforations, holes, or apertures 15 extend through the substrate 1. The perforations, holes, or apertures 15 may provide for air flow communication through the sensing element 10 and may improve particle contact with the sensing element 10 or improve the fluid dynamics of the fluid near the electrode pair A, B.

A protective film or removable liner (not shown) may be removably adhered to the sensing element 10 to provide protection during transport and installation of the sensing element 10 and electrode pair structures 2, 4. The sensing element 10 may be applied to a respirator or personal protective device or element, as described below.

Figure 15:
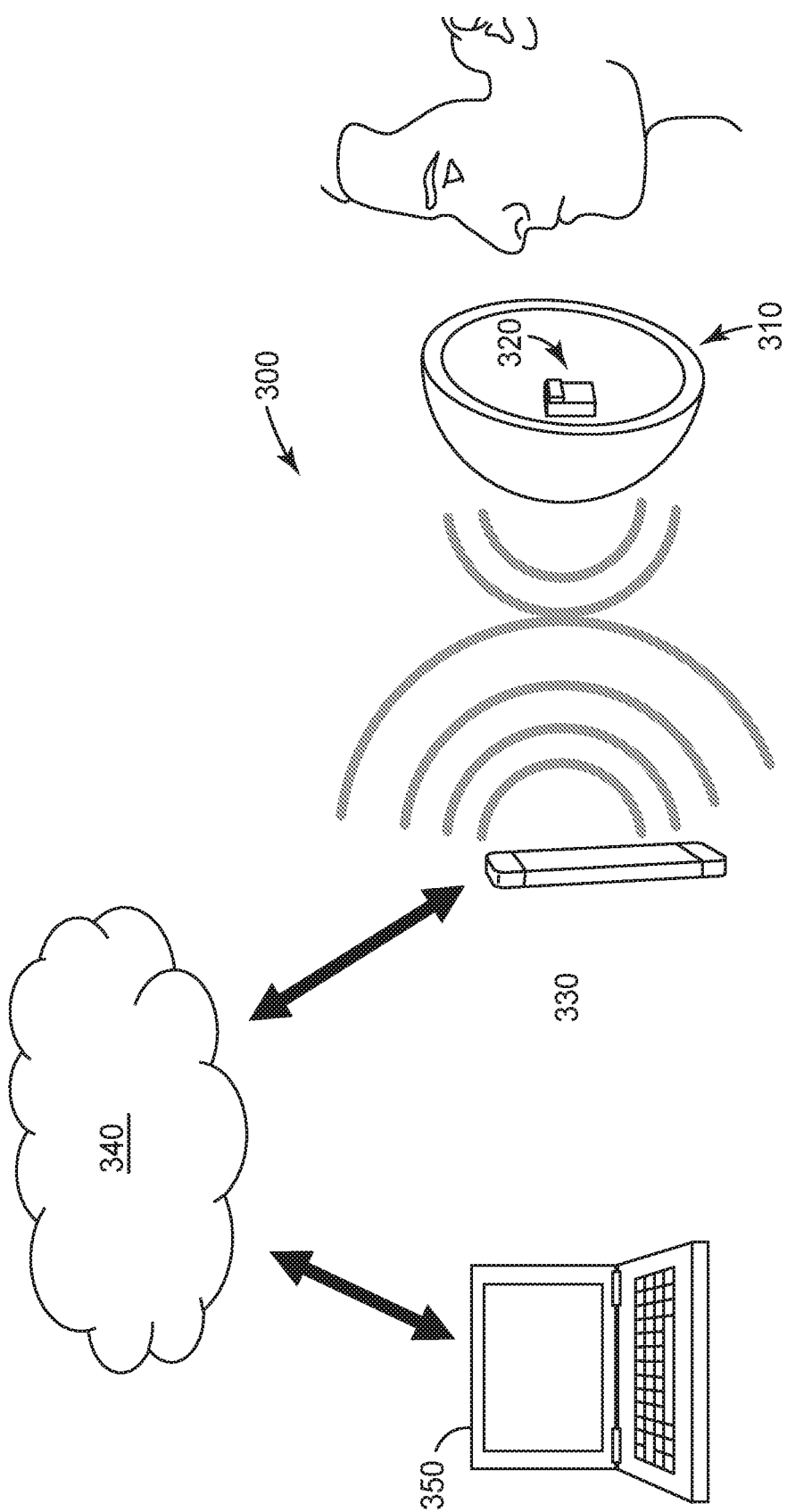
FIG. 15 is a schematic diagram of an illustrative respirator sensor system.

FIG. 15 is a schematic diagram of an illustrative respirator sensor system 300. The system 300 includes a respirator 310, a sensor 320 including a sensing element (as described herein), and a reader 330 configured to be in wireless communication with the sensor 320. The sensor 320 is positioned substantially into an interior gas space of the respirator 310.

The respirator sensor system 300 may be configured to detect the presence of unfiltered air within the interior gas space of the respirator 310. The respirator sensor system 300 may be configured to detect the leakage of unfiltered air within the interior gas space of the respirator 310.

As described above, the sensing element is configured to sense fluid-soluble particulate matter when a liquid layer is disposed in a gap on at least a part of the surface of the sensing element. Fluid ionizable particles may at least partially dissolve and may at least partially ionize in the liquid layer, resulting in a change in an electrical property between at least two of the electrodes.

Water vapor may be produced by human breath inside of the respirator and condense onto the high surface energy region of the sensing element and form the liquid layer. In an example, salt aerosol particles, such as sodium chloride, may come into contact with this condensed water vapor so that the salt particle dissolves and alters an electrical property (for example, impedance) of at least one of the electrode pairs. This change in electrical property may be sensed by the sensor 320 and wirelessly communicated to a remote reader 330. The transport of the fluid ionizable particulate matter to the sensing element may be affected by human breath.

The sensing element is a fluid ionizable detection element that may be configured such that the condensing vapor does not condense uniformly on the surface of the sensing element, as described above. The fluid ionizable detection element may be further configured such that the condensed vapor in contact with at least one electrode does not form a continuous condensed phase to at least one other electrode.

The respirator 310 may be any personal protective respirator article such as a filtering facepiece respirator or elastomeric respirator, for example. The sensor 320 may include a power source, communication interface, sensing electronics, and antenna. The sensor 320 power source may be a battery, a rechargeable battery, or energy harvester.

The sensing element may be configured to be replaceable and mechanically separable from the sensor 320. The sensing element may be in removable communication with the sensor 320. The sensor 320 may be reusable by replacing a used or spent sensing element with a fresh or new sensing element.

The sensor 320 may be fixed to, or adhered to, or connected to an interior surface of the respirator 310 or personal protective device or element. The interior surface may define a interior gas space of the respirator once the respirator 310 or personal protective device or element is worn by a user. The interior gas space is in airflow communication with the breath of the user wearing the respirator 310 or personal protective device or element. The sensor 320 may be removably positioned or attached within the interior gas space. The sensor 320 may be removably positioned or attached to the interior surface of the respirator 310.

The sensor 320 may be fixed to, or adhered to, or connected to an interior surface of the respirator 310 by any useful attachment system, such as, adhesive, hook and loop or suction, for example. The sensor attachment system may not penetrate the thickness of the interior surface of the respirator 310, the sensor attachment system may not extend through the thickness of the interior surface of the respirator 310, the sensor attachment system may not be in contact with an exterior surface of the respirator 310. The sensor attachment system may not penetrate a surface of the respirator in contact with an exterior gas space.

The size and weight of the sensor 320 are selected such that the sensor does not interfere with a wearer's use of the respirator 310. The size of the sensor 320 and a weight of the sensor 320 are selected such that the sensor 320 does not alter the fit the respirator 310 on a wearer. The sensor 320 may have a weight in a range from 0.1 to 225 grams, preferably less than 10 grams, or from 1 to 10 grams. A sensor weighing 225 grams may not alter the fit of the respirator if the respirator is sufficiently tight, but lower weights are preferred so as to reduce the weight of the respirator. The sensor 320 may have a volume in a range from 0.1 to 50 $cm^3$, preferably less than 10 $cm^3$, or from 1 to 10 $cm^3$.

The sensor 320 may wirelessly communicate with a remote reader 330. The sensor 320 may wirelessly communicate data to the reader 330 regarding changes in an electrical property of the sensing element. The communication between the reader 330 and the sensor 320 is via electromagnetic communication, such as via magnetic field, or Near Field Communication, or Bluetooth Low Energy, or optical illumination and detection, WiFi, Zigbee, or the like.

The sensor 320 may and reader 330 may communicate with one another about one or more constituents of a gas or aerosol within the interior gas space. The sensor 320 may and reader 330 may communicate with one another about physical properties related to a gas within the interior gas space, such as temperature, pressure, humidity, and the like. The sensor 320 may and reader 330 may communicate with one another about parameters used to assess physiological conditions of a wearer of the respirator.

The reader 330 may include a power source, communication interface, control electronics, and antenna. The reader 330 may wirelessly communicate with a remote device 350 via the internet 340. The reader 330 may communicate with the internet 340 via wireless connection. The reader 330 may communicate with the internet 340 via direct wired communication. The remote device 350 may include any of memory, data storage, control software, or at least one processor to receive and utilize the data or information provided by the reader 330 directly or via the internet 340.

The respirator sensor system 300 may be utilized to detect fluid ionizable particles in a gaseous medium. The method includes contacting a gaseous medium with a fluid ionizable particulate matter sensing element, and condensing a component of the gaseous medium on at least a portion of the fluid ionizable particulate matter sensing element; and determining an electrical property at a first point in time between a pair of electrodes of the fluid ionizable particulate matter detection element; and determining an electrical property at a second point in time between a pair of electrodes of the fluid ionizable particulate matter detection element; and determining a value related to the presence of fluid ionizable particles in the gaseous medium at least partially by comparing the value of the electrical property at the first point in time to the electrical property at the second point in time.

The respirator sensor system 300 may be utilized to detect fluid ionizable particles in a gaseous medium. The method includes contacting a gaseous medium with a fluid ionizable particulate matter sensing element, and condensing a component of the gaseous medium on at least a portion of the fluid ionizable particulate matter sensing element; and determining an electrical property at a first frequency, such as 1 Hz, between a pair of electrodes of the fluid ionizable particulate matter detection element; and determining an electrical property at a second frequency, such as 100 kHz, between a pair of electrodes of the fluid ionizable particulate matter detection element; and determining a value related to the presence of fluid ionizable particles in the gaseous medium at least partially by comparing the value of the electrical property at the first frequency to the electrical property at the second frequency. The frequency may include DC.

The respirator sensor system 300 may include an additional computing system or remote device 350 wherein data is communicated between the respirator sensor system 300 and the additional computing system or remote device 350. In some embodiments, the additional computing system is a cloud computing architecture. The communication between the reader 330 and the additional computing system or remote device 350 may be via a wired connection or via wireless internet network. The additional computing system or remote device 350 may record data transmitted by the reader 330. The additional computing system or remote device 350 may process data transmitted by the reader 330, and communicate information back to the reader 330.

The respirator sensor system 300 may be utilized to detect fluid ionizable particles in a gaseous medium. The method includes contacting a gaseous medium with a fluid ionizable particulate matter sensing element, and condensing a component of the gaseous medium on at least a portion of the fluid ionizable particulate matter sensing element; and determining an electrical property between a first pair of electrodes of the fluid ionizable particulate matter detection element; and determining an electrical property between a second pair of electrodes of the fluid ionizable particulate matter detection element; and determining a value related to the presence of fluid ionizable particles in the gaseous medium at least partially by comparing the value of the electrical property of the first pair of electrodes to the electrical property of the second pair of electrodes.

The method may include the second pair of electrodes utilized as a reference electrode. The reference electrode may be an analyte reference electrode. The reference electrode may be isolated from a target component of the gaseous medium. The target component of the gaseous medium may be a fluid ionizable particle, such as a salt, for example.

The respirator sensor system 300 may be utilized to provide real-time feedback on the quality of the respirator fit. The respirator sensor system 300 may be utilized to provide a method of fit testing. The fit testing method includes providing a respirator, then providing a sensor including a sensing element removably positioned substantially within an interior gas space of the respirator, then providing a reader configured to be in wireless communication with the sensor; and positioning the respirator over a mouth and a nose of a user while the sensor is positioned substantially within an interior gas space of the respirator; and observing respirator fit assessment data communicated from the sensor to the reader.

The respirator sensor system 300 may be utilized with a computer vision tool or camera to assure a consistent quality of the respirator fit. The method includes: 1) The respirator wearer undergoes respirator fit testing while standing in front of a camera. The fit test is conducted with the selected respirator model equipped with wireless aerosol sensor described herein. 2) The sensor measures aerosol leakage into the respirator in real time as the worker adjusts the respirator to fit his/her face. 3) Once the measured aerosol leakage drops below accepted threshold ensuring proper fit, the wireless sensor automatically signals the camera to capture the image of the respirator in its correct fit position on the worker's face. 4) The captured image is analyzed and saved to be used as reference in the future whenever the worker dons a respirator, to ensuring consistent respirator fit position on the worker's face. The image may be captured at any point during the test, such as before the test begins, to be subsequently linked to the fit value determined by the wireless aerosol sensor system.

The term "fit position" describes the configuration, position and orientation of the respirator on the user's face. Fit position includes position of nose clip, shape of nose clip, position of straps, orientation on the face. An imaging sensor may include a traditional RGB sensor and may also include a NIR camera, depth sensor, and the like.

The worker may compare the "fit position" image with the current placement of the respirator on the worker's face. Adjustment to the respirator fit may be made until the "fit position" matches or substantially matches the current placement of the respirator on the worker's face.

Objects and advantages of this disclosure are further illustrated by the following examples, but the particular materials and amounts thereof recited in these examples, as well as other conditions and details, should not be construed to unduly limit this disclosure.

EXAMPLES

All parts, percentages, ratios, etc. in the examples are by weight, unless noted otherwise. Solvents and other reagents used were obtained from Sigma-Aldrich Corp., St. Louis, Mo. unless specified differently.

Sodium Chloride Aerosol Sensor

Sensor elements were constructed according to the method described in FIG. 5A and FIG. 5B and evaluated for respirator fit testing applications.

The electrical impedance of a medium is a function of the number of mobile charge carriers in the medium, the unit charge of the carriers, as well as their opposition to motion induced by coulombic forces. As a result, the electrical impedance of a liquid solvent with a dissolved ionic solute is generally a function of the concentration of the solute. A sensing element, such as the one described above, may be used to probe the electrical impedance of a medium by contacting the electrodes with the medium and monitoring the resistance to an applied electric field. In fluid media, such as water, the electric field is typically an alternating field at a prescribed frequency which can provide both resistive and reactive impedance information.

Figure 11:
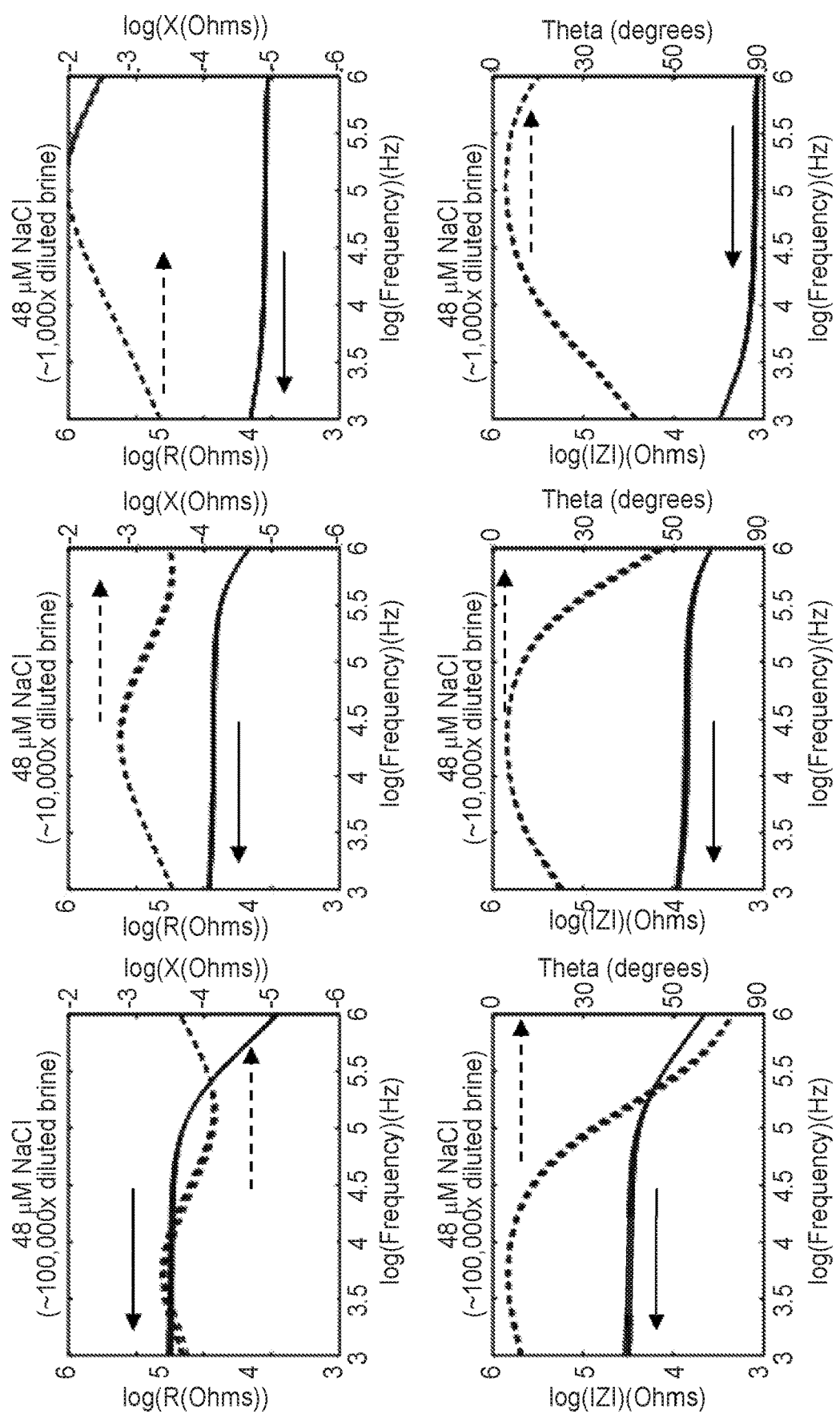
FIG. 11 are graphs illustrating the sensor response to different concentrations of NaCl in water, the top three graphs illustrate the resistance (solid lines) and reactance (dashed lines), as a function of frequency, measured by the sensor when coated with a liquid layer of the solution indicated. The bottom three graphs illustrate the impedance magnitude (solid lines) and phase shift (dashed lines), as a function of frequency, measured by the sensor when coated with a liquid layer of the solution indicated. Z=impedance magnitude, Theta=phase shift, R=resistance, and X=reactance.

As an example, FIG. 11 shows the electrical impedance, specifically the impedance magnitude, phase shift, resistance and reactance as a function of frequency, of a sensing element such as the one described above when immersed in water/sodium chloride solutions of different concentrations. FIG. 11 top row are graphs illustrating the sensor response to different concentrations of NaCl in water, the resistance (solid lines) and reactance (dashed lines), as a function of frequency, measured by the sensor when coated with a liquid layer of the solution indicated. R=resistance, X=reactance. FIG. 11 bottom row are graphs illustrating the sensor response to different concentrations of NaCl in water, corresponding impedance magnitude (solid lines) and phase shift (dashed lines), as a function of frequency, measured by the sensor when coated with a liquid layer of the solution indicated. Z=impedance magnitude, Theta=phase shift.

The impedance data is recorded by a Precision Impedance Analyzer 4294A available from Agilent, USA. A significant decrease in the impedance magnitude and resistance of the media (plotted on a log scale) is seen with an increase in conductivity, as well as shifts in the overall profile of all the curves. While this example is a case of a liquid media and not an aerosol, the underlying mechanism of the measurement forms the basis of how the sensors described in this application may be used to measure solution ionizable aerosols, as described below.

Figure 12A:
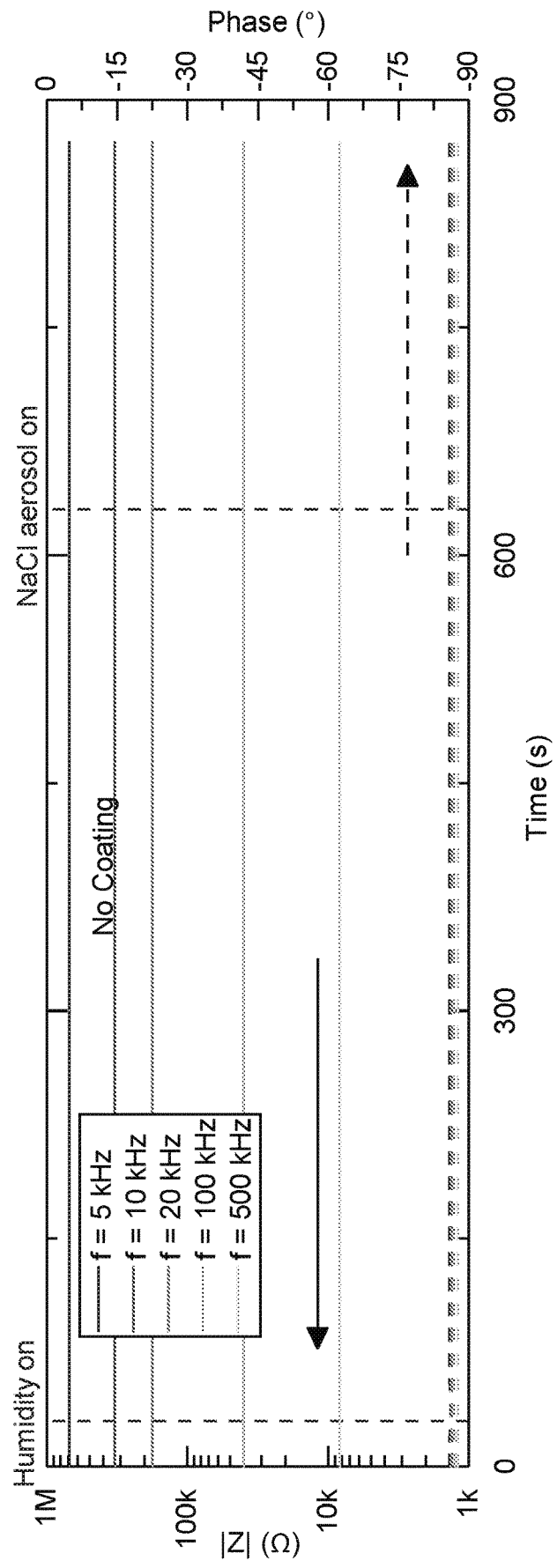
FIG. 12A-12C are graphs that illustrate a comparison of isothermal water uptake and NaCl aerosol response for different surface modification and coating systems applied to salt aerosol sensor.
Figure 12B:
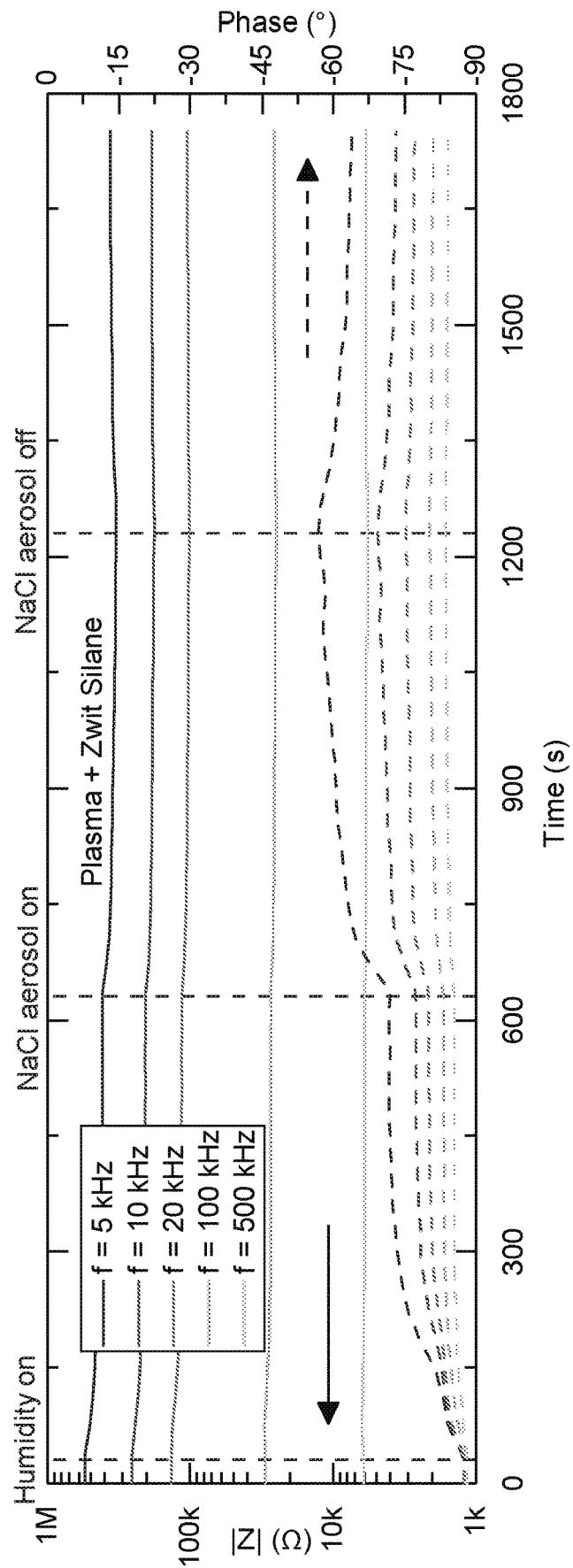
Figure 12C:
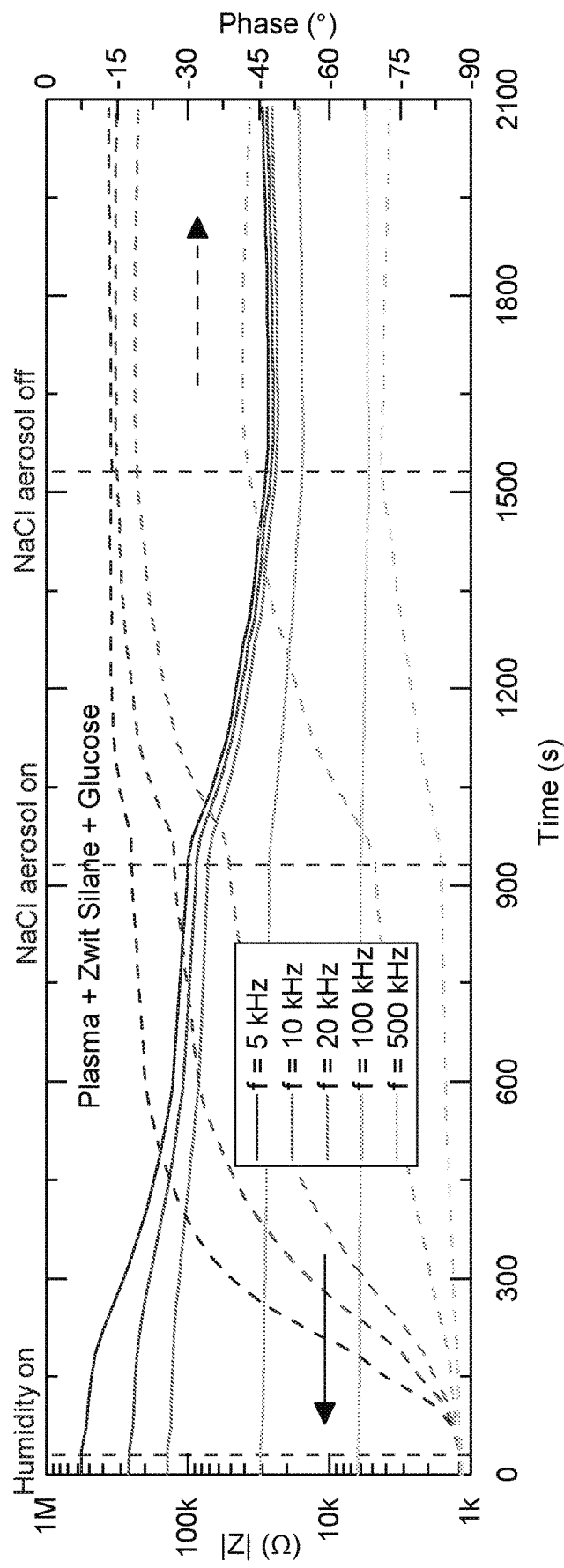
Figure 13A:
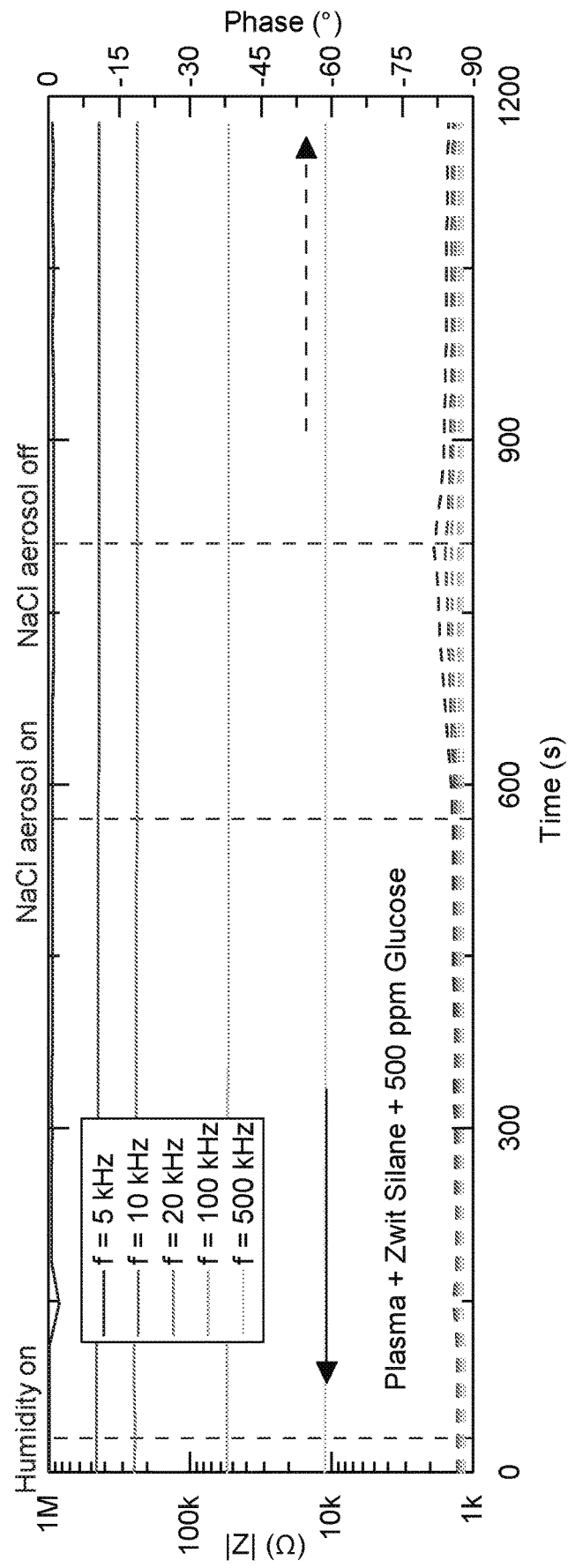
Figure 13C:
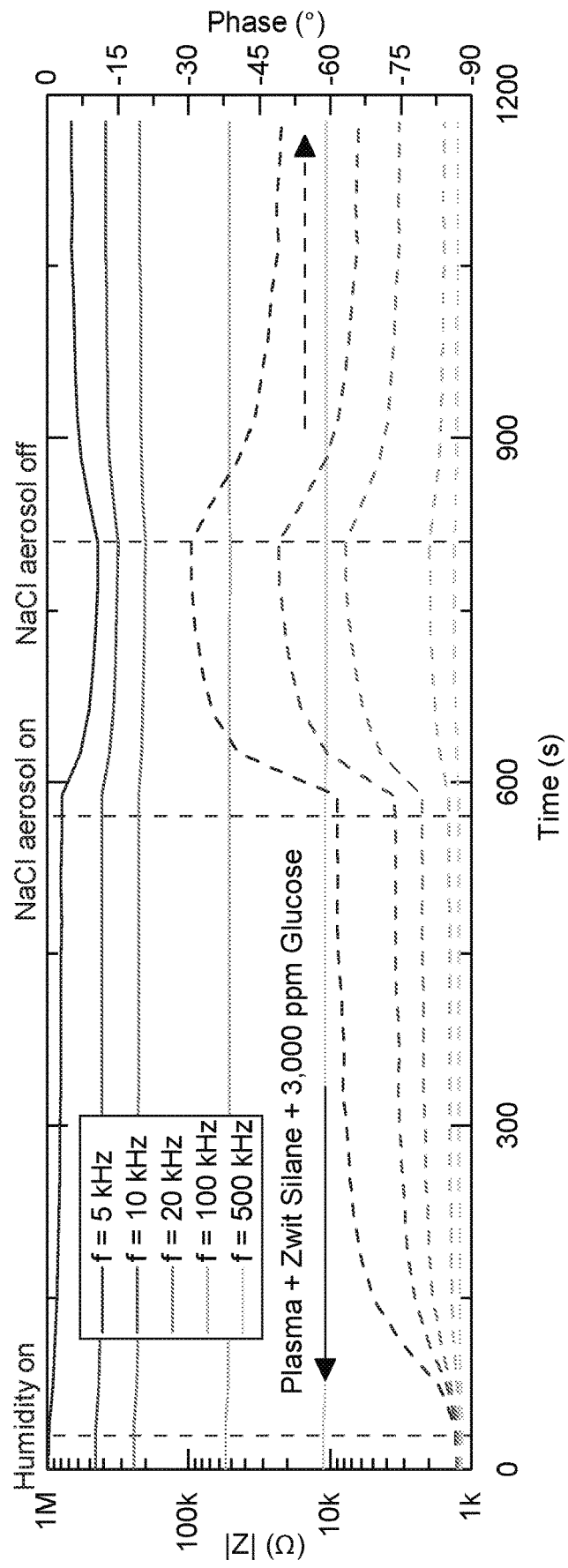
Figure 13D:
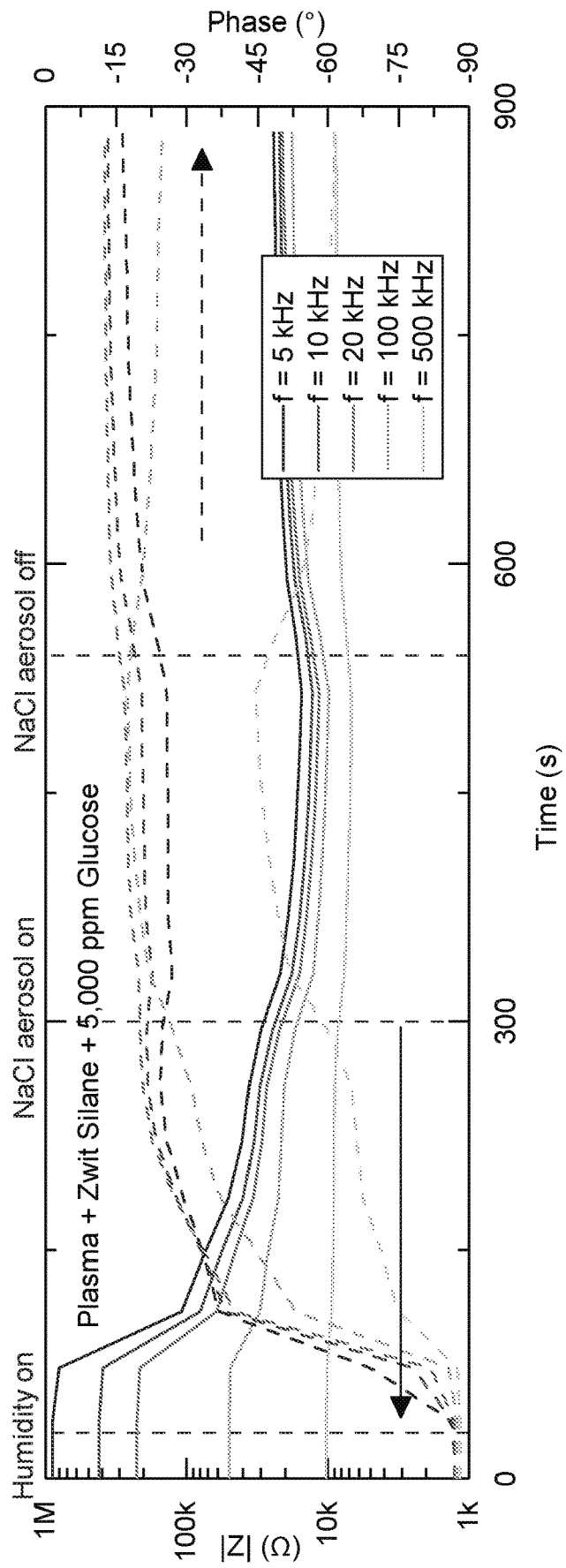

The compositions described thus far may be configured to alter the performance of a fluid ionizable aerosol sensing element. Exemplary data that illustrates the principal is shown in FIG. 12A-12C. FIG. 12A-12C are graphs that illustrate a comparison of isothermal water uptake and NaCl aerosol response for different surface modification and coating systems applied to a salt aerosol sensor.

The setup for the experiment used to generate the data in FIG. 12A-12C is as follows: a fluid ionizable sensing element, with a pair of interdigitated conducting electrodes on the surface, is connected to an electrical impedance spectrum analyzer. At t=0, the impedance spectrum recording of the sensor begins. At t=60 s, the sensor is placed into a test chamber which is flowing air at 15 liters per minute, with approximately 95% relative humidity. The sensing element is in fluid contact with a portion of the flow. At the indicated time in each plot ('NaCl aerosol on'), an aerosol containing approximately 10 μg/L NaCl aerosol, with a mass mean particle diameter of 2 micrometers, is introduced in the flow stream. The aerosol stream is generated by atomizing a NaCl/water solution of approximately 5 wt % NaCl using an atomizer. The aerosol stream is then removed at the indicated time ('NaCl aerosol off').

For the duration of the experiment, the sensing element is approximately in thermal equilibrium with the air stream, and the temperature of the airstream is constant. FIG. 12A shows the response of an exemplary sensing element with no surface modification to change the surface energy, FIG. 12B shows that of a sensing element with the plasma+zwitterionic silane surface modification (described in FIG. 5A), and FIG. 12C that of a sensing element with the plasma+zwitterionic silane surface modification with an additional glucose layer (as described in FIG. 5B).

FIG. 12A illustrates the sensing element with no surface modification or coating layer shows no significant change in electrical impedance at any point during the experiment.

This sensing element with no modification does not have a strong affinity to form a fluid layer on the surface, and therefore lacks a strong mechanism in which the NaCl aerosol particles may ionize on the sensing element.

FIG. 12B illustrates that the sensing element with only plasma+zwitterionic silane treatment results in a small decrease in impedance in response to humid air, and an additional decrease throughout the duration of NaCl aerosol exposure. A small increase in impedance once the aerosol stream is removed is likely due to a small change in humidity introduced by the NaCl aerosol stream.

This sensing element with only the plasma+zwitterionic silane treatment enables a hydrophilic surface on the electrodes, which promotes some amount of fluid condensation, however at thermal equilibrium, the driving force for fluid formation on the surface is lower than that of the sensing element with the additional hygroscopic material layer (FIG. 12C).

FIG. 12C illustrates the sensing element with plasma+zwitterionic silane surface treatment and also the glucose layer shows a much more significant response to the humid air stream, and then to the NaCl aerosol stream. This is due to the hygroscopic property changes of the sensing element introduced by the addition of the glucose (hygroscopic material) layer.

An example of how changing the coating weight of the hygroscopic material layer may impact the sensing element response is shown in FIG. 13A-13D, which illustrates the results of an experiment similar to that of FIG. 12C, with variations in hygroscopic layer coating weight. FIG. 13A-13D are graphs that illustrate a comparison of isothermal water uptake and NaCl aerosol response for O2+TMS plasma+zwitterionic silane followed by different coat weights of glucose applied to the salt aerosol sensor.

Figure 14A:
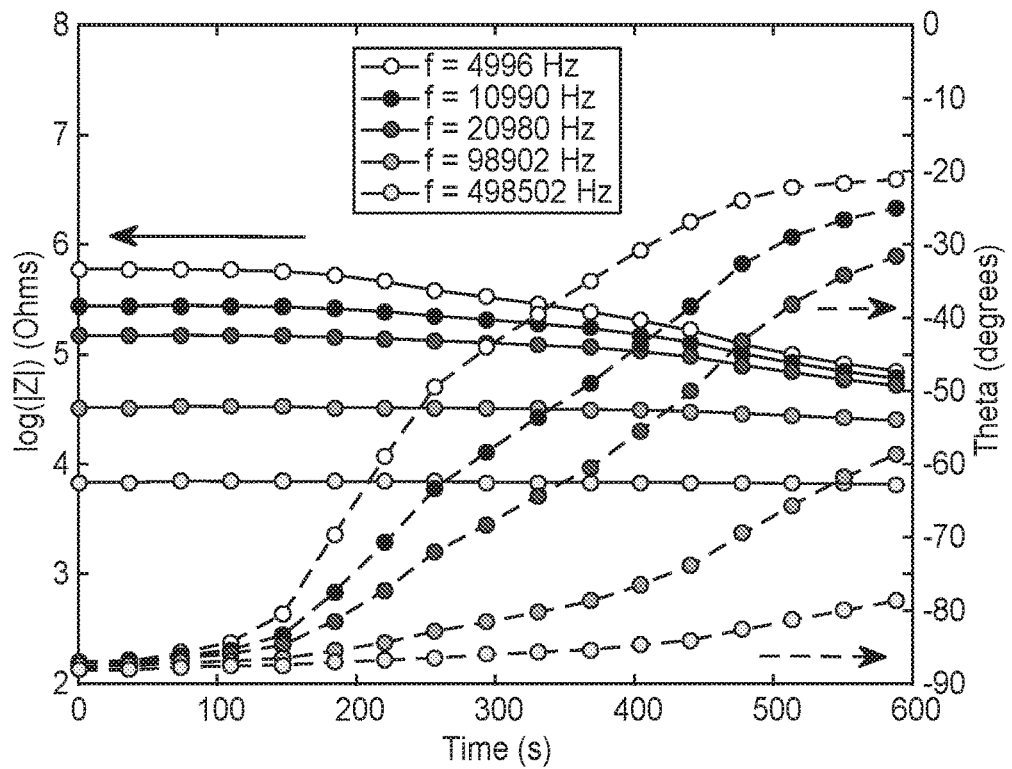
FIG. 14A-14C are graphs that illustrate a comparison of isothermal water uptake and NaCl aerosol response for sensors with and without a filter element.
Figure 14B:
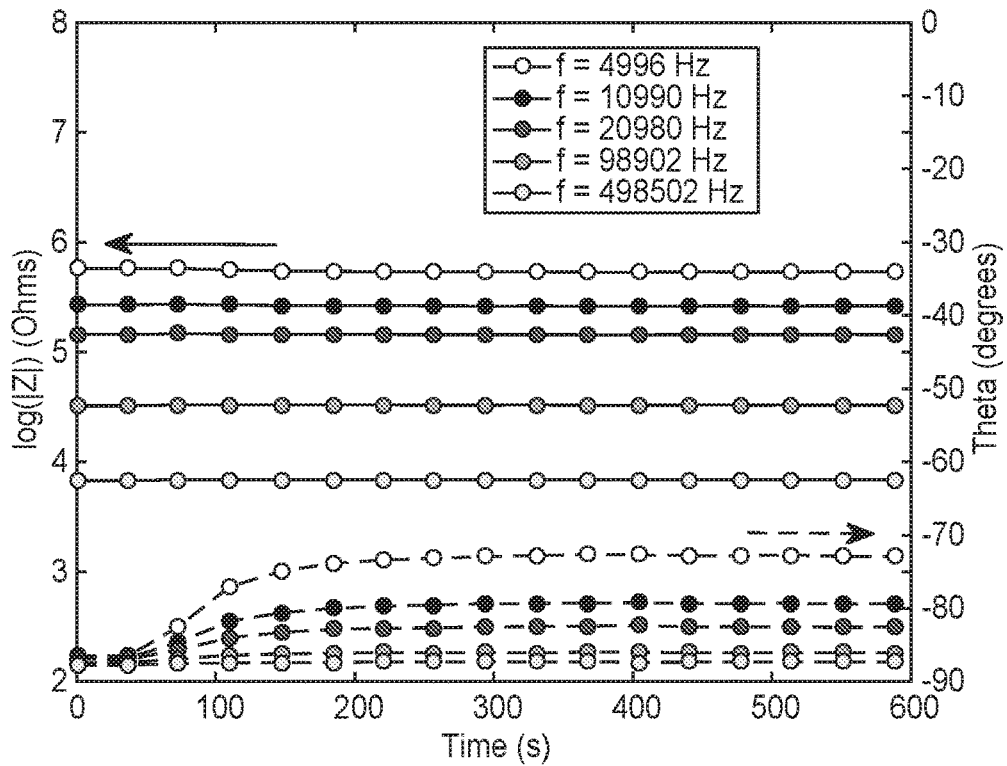
Figure 14C:
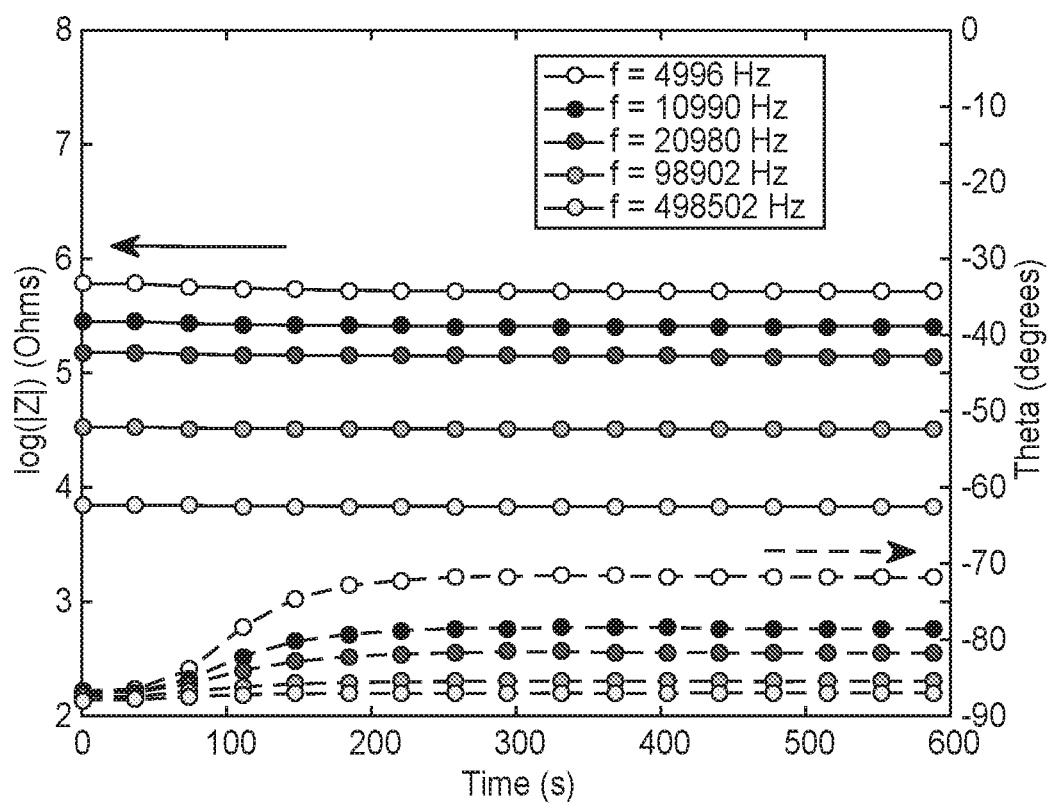

FIG. 14A-14C are graphs that illustrate a comparison of isothermal water uptake and NaCl aerosol response for sensors with and without a filter element. An example of how a particulate filter may be used to create a reference electrode pair, as described in FIG. 7 and FIG. 8, is shown by the data in FIG. 14A-14C.

All tests are conducted with the sensing element in the flow stream of a humidity controlled NaCl aerosol system. The aerosol is generated by atomized a solution of 5 wt % NaCl in water using an atomizer. The humidity of all tests is between 95% RH and 100% RH. The sensing element in all tests is an interdigitated array, with 5 mil line/space widths of the digits, with ~0.5 $cm^2$ area. The graphs show the impedance magnitude (solid lines) and phase shift (dashed lines) over time at five different frequencies. The impedance data is recorded by a Precision Impedance Analyzer 4294A available from Agilent, USA.

For example, FIG. 14A shows the response of a sensing element, substantially similar to those described in this application, with no particulate filter, which is inserted into an airstream containing aerosolized sodium chloride microparticles and nanoparticles.

FIG. 14B shows a similar experiment, where the aerosolized solution does not contain sodium chloride, such that aerosolized solution produces only water vapor without sodium chloride particles.

FIG. 14C shows the result of the same experiment as that in FIG. 14A, except that the sensing element is configured with a particulate filter as described previously. The similarities of the response shown in FIG. 14B and FIG. 14C demonstrate that the particulate filter adequately allows the fluid components, such as water vapor, to contact the reference electrode pair, but prevents the particulate matter from contacting the reference electrode pair.

Thus, embodiments of SENSING SYSTEM FOR RESPIRATOR are disclosed.

All references and publications cited herein are expressly incorporated herein by reference in their entirety into this disclosure, except to the extent they may directly contradict this disclosure. Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof. The disclosed embodiments are presented for purposes of illustration and not limitation.

What is claimed is:

1. A system comprising:
a respirator;
a sensor comprising a sensing element, wherein the sensor is positioned substantially within an interior gas space of the respirator, and
a reader configured to be in wireless communication with the sensor
wherein the system is configured to detect leakage of unfiltered air containing a fluid-soluble particulate matter into the interior gas space by sensing a change in an electrical property of the sensing element when exposed to the fluid-soluble particulate matter.

2. The system according to claim 1, wherein a size of the sensor and a weight of the sensor are selected such that the sensor does not interfere with a wearer's use of the respirator.

3. The system according to claim 1, wherein a size of the sensor and a weight of the sensor are selected such that the sensor does not alter the fit the respirator on a wearer.

4. The system according to claim 1, wherein the sensor is in electrical communication with the sensing element and the sensor senses a change in an electrical property of the sensing element.

5. The system according to claim 1, wherein the sensing element is configured to sense fluid-soluble particulate matter when a liquid layer is disposed in a gap on at least a part of the surface of the sensing element, wherein a fluid ionizable particle may at least partially dissolve and may at least partially ionize in the liquid layer, resulting in a change in an electrical property between at least two electrodes of the sensing element.

6. The system according to claim 1, wherein the sensor is removably positioned within the interior gas space.

7. The system according to claim 1, wherein the sensing element is in removable communication with the sensor.

8. The system according to claim 1, wherein the communication between the reader and the sensor is via electromagnetic communication.

9. The system according to claim 8, wherein the electromagnetic communication is via magnetic field.

10. The system according to claim 8, wherein the electromagnetic communication is via Near Field Communication.

11. The system according to claim 8, wherein the electromagnetic communication is via Bluetooth Low Energy.

12. The system according to claim 8, wherein the electromagnetic communication is via optical illumination and detection.

13. The system according to claim 1, wherein the sensor and reader communicate with one another about one or more constituents of a gas or aerosol within the interior gas space.

14. The system according to claim 1, wherein the sensor and reader communicate with one another about physical properties related to a gas within the interior gas space.

15. The system according to claim 1, wherein the sensor and reader communicate parameters used to assess physiological conditions of a wearer of the respirator.

16. The system according to claim 5, wherein at least one component of the liquid layer is provided by human breath.

17. The system according to claim 5, wherein interaction of the fluid ionizable particle with the sensing element is at least partially influenced by human breath.

18. The system according to claim 1, wherein the sensing element is configured to be mechanically separable from the sensing device.

* * * * *